United States Patent
Han et al.

(10) Patent No.: US 9,545,567 B2
(45) Date of Patent: Jan. 17, 2017

(54) APPARATUS AND METHOD FOR MANIPULATING A VIRTUAL WORLD BY UTILIZING BIOMETRIC INFORMATION

(75) Inventors: Seung Ju Han, Yongin-si (KR); Jae Joon Han, Yongin-si (KR); Won Chul Bang, Yongin-si (KR); Do Kyoon Kim, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 805 days.

(21) Appl. No.: 13/810,531

(22) PCT Filed: Jun. 14, 2011

(86) PCT No.: PCT/KR2011/004346
§ 371 (c)(1),
(2), (4) Date: Mar. 29, 2013

(87) PCT Pub. No.: WO2012/011665
PCT Pub. Date: Jan. 26, 2012

(65) Prior Publication Data
US 2013/0178289 A1 Jul. 11, 2013

(30) Foreign Application Priority Data

Jul. 20, 2010 (KR) .......................... 10-2010-0070135
Oct. 6, 2010 (KR) .......................... 10-2010-0097267
Mar. 18, 2011 (KR) .......................... 10-2011-0024289

(51) Int. Cl.
*G06F 19/00* (2011.01)
*A63F 13/212* (2014.01)
(Continued)

(52) U.S. Cl.
CPC .............. *A63F 13/212* (2014.09); *A61B 5/00* (2013.01); *A61B 5/02055* (2013.01);
(Continued)

(58) Field of Classification Search
CPC ............................. A63F 13/00; A63F 13/212
(Continued)

(56) References Cited

U.S. PATENT DOCUMENTS 5,293,187 A * 3/1994 Knapp et al. ............... 351/210
8,382,590 B2 * 2/2013 Stivoric et al. ............. 463/36
(Continued)

FOREIGN PATENT DOCUMENTS

CN 1719385 A 1/2006
JP 11-164966 A 6/1999
(Continued)

OTHER PUBLICATIONS

Chinese Office Action issued on Dec. 17, 2014, in counterpart Chinese Application No. 201180035744.1 (12 pages in English, 8 pages in Chinese).
(Continued)

*Primary Examiner* — Reginald Renwick
(74) *Attorney, Agent, or Firm* — NSIP Law

(57) ABSTRACT

An apparatus and method for processing a virtual world. According to certain embodiments of the present disclosure, real-world biometric information on the user may be collected using a bio sensor, and the collected information may be controlled based on the sensor characteristics of the bio sensor, thereby enabling interaction between the real world and the virtual world, as well as between virtual worlds. In addition, an interactive game which is executed in the virtual world on the basis of the collected biometric information may be controlled to thereby produce a virtual world having enhanced realism. Moreover, the real-world health status of a user may be determined and displayed on the basis of the collected biometric information, thereby enabling the health status of the user to be seen.

30 Claims, 15 Drawing Sheets

(51) Int. Cl.
*A61B 5/00* (2006.01)
*A61B 5/0205* (2006.01)
*A61B 5/0452* (2006.01)
*A61B 5/021* (2006.01)
*A61B 5/024* (2006.01)
*A61B 5/0476* (2006.01)
*A61B 5/053* (2006.01)
*A61B 5/107* (2006.01)
*A61B 5/145* (2006.01)

(52) U.S. Cl.
CPC ............ *A61B 5/0452* (2013.01); *A61B 5/021* (2013.01); *A61B 5/024* (2013.01); *A61B 5/0476* (2013.01); *A61B 5/0533* (2013.01); *A61B 5/1072* (2013.01); *A61B 5/14542* (2013.01); *A63F 2300/1012* (2013.01); *G06F 19/3437* (2013.01)

(58) Field of Classification Search
USPC ..................................................... 463/30, 36
See application file for complete search history.

(56) References Cited

U.S. PATENT DOCUMENTS

| | | | | |
|---|---|---|---|---|
| 2004/0005924 | A1* | 1/2004 | Watabe et al. ................. | 463/36 |
| 2006/0217598 | A1* | 9/2006 | Miyajima et al. ............ | 600/300 |
| 2008/0318678 | A1* | 12/2008 | Stivoric ............ | G06F 17/30598 463/36 |
| 2009/0325701 | A1* | 12/2009 | Andres Del Valle ........... | 463/36 |
| 2011/0009193 | A1* | 1/2011 | Bond et al. ..................... | 463/36 |

FOREIGN PATENT DOCUMENTS

| | | |
|---|---|---|
| JP | 2000-24324 A | 1/2000 |
| JP | 2001-34785 | 2/2001 |
| JP | 2002-18135 A | 1/2002 |
| JP | 2006-294024 | 10/2006 |
| KR | 10-0493714 | 5/2005 |
| KR | 10-2006-0071295 | 6/2006 |
| KR | 10-2008-0004196 | 1/2008 |
| KR | 10-2009-0067822 | 6/2009 |
| KR | 10-2009-0096051 | 9/2009 |
| WO | WO 2006/011076 A1 | 2/2006 |
| WO | WO 2007/045021 A1 | 4/2007 |
| WO | WO 2008/099288 A2 | 8/2008 |
| WO | WO 2010/022882 A2 | 3/2010 |
| WO | WO 2010/045385 A2 | 4/2010 |

OTHER PUBLICATIONS

International Search Report of Corresponding PCT Application PCT/KR2011/004346 mailed Feb. 6, 2012.

Japanese Office Action mailed Jan. 20, 2015 in counterpart Japanese Application No. 2013-520636 (4 pages, in Japanese, with partial English translation of the substantive portion).

Extended European Search Report issued on May 12, 2015 in counterpart European Application No. 11809792.2 (7 pages in English).

* cited by examiner

FIG. 6

| | 600 |
|---|---|
| Diagram 610 | ⊟ grp sidccmd:Sensor Capability Base Attributes<br>601 — unit<br>602 — maxValue<br>603 — minValue<br>604 — offset<br>605 — numOflevels<br>606 — sensitivity<br>607 — SNR<br>608 — accuracy |
| Attributes 620 | \<unit\>\<maxValue\>\<minValue\>\<offset\>\<numOflevels\>\<sensitivity\>\<SNR\>\<accuracy\> |
| Source 630 | \<!-- ################################################ --\><br>\<!-- Definition of SDC Base Attributes --\><br>\<!-- ################################################ --\><br>\<attributeGroup name="SensorCapabilityBaseAttributes"\><br>  \<attribute name="unit" type="cid:unitType" use="optional"/\><br>631 — \<attribute name="maxValue" type="float" use="optional"/\><br>632 — \<attribute name="minValue" type="float" use="optional"/\><br>  \<attribute name="offset" type="float" use="optional"/\><br>633 — \<attribute name="numOflevels" type="nonNegativeInteger" use="optional"/\><br>  \<attribute name="sensitivity" type="float" use="optional"/\><br>  \<attribute name="SNR" type="float" use="optional"/\><br>  \<attribute name="accuracy" type="float" use="optional"/\><br>\</attributeGroup\> |

| Diagram | SensorAdaptation PreferenceBaseType — ⊟ attributes — ⊟ grp sidccmd:SensorAdaptation PreferenceBaseAttributes — any ##other |
|---|---|
| Attributes | `<SensorAdaptationPreferenceBaseAttributes><anyAttribute>` |
| Source | `<!-- ############################################## -->`<br>`<!-- Sensor Preference base type                 -->`<br>`<!-- ############################################## -->`<br>`<complexType name="SensorAdaptationPreferenceBaseType" abstract="true">`<br>`  <complexContent>`<br>`    <extension base="dia:UserCharacteristicBaseType">`<br>`      <attributeGroup ref="cid:SensorAdaptationPrefBaseAttributes"/>`<br>`      <anyAttribute namespace="##other" processContents="lax"/>`<br>`    </extension>`<br>`  </complexContent>`<br>`</complexType>` |

810 — Diagram
820 — Attributes
830 — Source

| | |
|---|---|
| Diagram 910 | ⊟ grp sidccmd:SensorAdaptationPreferenceBaseAttributes<br>901 → SensorIdRef<br>902 → SensorAdaptationMode<br>903 → activate<br>904 → unit<br>905 → maxValue<br>906 → minValue<br>907 → numOflevels |
| 920 | |
| Attributes | <SensorIdRef><SensorAdaptationMode><activate><unit><maxValue><minValue><numOflevels> |
| Source 930 | <!-- ################################# --><br><!-- SensorAdaptation Preference Base Attributes --><br><!-- ################################# --><br><attributeGroup name="SensorAdaptationPrefBaseAttributes"><br>  <attribute name="SensorIdRef" type="anyURI" use="optional"/><br>  <attribute name="SensorAdaptationMode" type="cid:adaptationModeType" use="optional"/><br>931 → <attribute name="activate" type="boolean" use="optional"/><br>932 → <attribute name="maxValue" type="float" use="optional"/><br>933 → <attribute name="minValue" type="float" use="optional"/><br>934 → <attribute name="numOflevels" type="nonNegativeInteger" use="optional"/><br></attributeGroup><br><simpleType name="adaptationModeType"><br>  <restriction base="string"/><br>    <enumeration value="strict"/><br>    <enumeration value="scalable"/><br>  </restriction><br></simpleType> |

APPARATUS AND METHOD FOR MANIPULATING A VIRTUAL WORLD BY UTILIZING BIOMETRIC INFORMATION

CROSS-REFERENCE TO RELATED APPLICATIONS

This application is a U.S. National Phase application of International Application No. PCT/KR2011/004346, filed on Jun. 14, 2011, and which claims the priority benefit of Korean Patent Application No. 10-2010-0070135, filed on Jul. 20, 2010, in the Korean Intellectual Property Office, Korean Patent Application No. 10-2010-0097267, filed on Oct. 6, 2010, filed in the Korean Intellectual Property Office, and Korean Patent Application No. 10-2011-0024289, filed on Mar. 18, 2011, in the Korean Intellectual Property Office, the disclosures of each of which are incorporated herein by reference.

BACKGROUND

1. Field

Example embodiments of the following disclosure relate to a method and apparatus for processing a virtual world, and more particularly, to an apparatus and method for applying information about a real world to the virtual world.

2. Description of the Related Art

Currently, an interest in experience-type games has been increasing in the video gaming market, for example. MICROSOFT CORPORATION introduced "Project Natal" at the "E3 2009" Press Conference. "Project Natal" may provide a user body motion capturing function, a face recognition function, and a voice recognition function by combining MICROSOFT'S XBOX 360 game console with a separate sensor device consisting of a depth/color camera and a microphone array, thereby enabling a user to interact with a virtual world without a dedicated controller. In addition, SONY CORPORATION introduced "Wand" which is an experience-type game motion controller. The "Wand" enables interaction with a virtual world through input of a motion trajectory of a controller by applying, to the PLAYSTATION 3 game console, a location/direction sensing technology obtained by combining a color camera, a marker, and an ultrasonic sensor.

A real world and a virtual world may interact in two directions. For example, in one direction, data information obtained by a sensor in the real world may be reflected to the virtual world. In the other direction, data information obtained from the virtual world may be reflected to the real world using an actuator. Embodiments suggest a virtual world processing apparatus and method for applying data obtained through a sensor in the real world to the virtual world, to achieve the interaction between the real world and the virtual world.

SUMMARY

Additional aspects and/or advantages will be set forth in part in the description which follows and, in part, will be apparent from the description, or may be learned by practice of the invention.

Example embodiments of the present disclosure provide a virtual world processing apparatus for enabling interoperability between a virtual world and a real world or interoperability between virtual worlds, the virtual world processing apparatus including an input unit to receive an input of sensed information collected by a bio sensor with respect to biometrics of a user in the real world, and an adapting unit to adapt the sensed information, based on a sensor capability associated with a capability of the bio sensor.

Example embodiments of the present disclosure also provide an operating method of a virtual world processing apparatus for enabling interoperability between a virtual world and a real world or interoperability between virtual worlds, the method including receiving an input of sensed information collected by a bio sensor with respect to biometrics of a user in the real world, and adapting the sensed information, based on a sensor capability associated with a capability of the bio sensor.

Example embodiments of the present disclosure also provide a method for interacting between a real world and a virtual world, the method including: sensing information regarding a user in the real world using at least one bio sensor; adapting the sensed information based on at least one sensor capability that corresponds to the at least one bio sensor; and controlling at least one object in the virtual world based on the adapted sensed information.

According to example embodiments, by collecting biometric information about a user in a real world using a bio sensor, and adapting the collected information based on sensor capability of the bio sensor, interoperability between the real world and a virtual world or interoperability between virtual worlds may be implemented.

In addition, by controlling an experience-type game played in the virtual world, based on the collected biometric information, a more realistic virtual world may be implemented. In addition, by determining and displaying a health of the user in the real world, based on the collected biometric information, the health of the user may be verified.

BRIEF DESCRIPTION OF THE DRAWINGS

These and/or other aspects and advantages will become apparent and more readily appreciated from the following description of the embodiments, taken in conjunction with the accompanying drawings of which:

FIG. 6 illustrates a syntax of sensor capability base attributes, according to example embodiments.

FIG. 8 illustrates a syntax of a sensor adaptation preference base type, according to example embodiments.

FIG. 9 illustrates a syntax of sensor adaptation preference base attributes, according to example embodiments.

DETAILED DESCRIPTION

Figure 1:
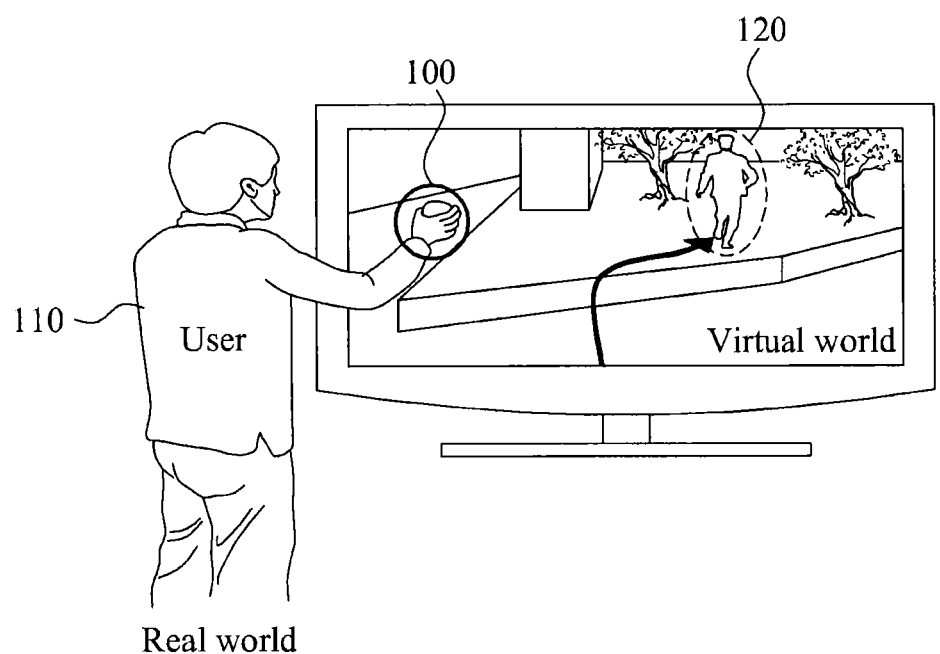
FIG. 1 illustrates an operation of controlling a virtual world object of a virtual world using a sensor, according to example embodiments.

Reference will now be made in detail to example embodiments, examples of which are illustrated in the accompanying drawings, wherein like reference numerals refer to the like elements throughout. Example embodiments are described below in order to explain example embodiments by referring to the figures.

FIG. 1 illustrates an operation of controlling a virtual world object of a virtual world using a sensor in a real world, according to example embodiments.

Referring to FIG. 1, a user 110 in a real world may manipulate an object 120 of the virtual world using a sensor 100 in the real world. The user 110 may input information relating to his or her motion, state, intention, shape, and the like, through the sensor 100. The sensor 100 may transmit control information (CI) related to the motion, state, intention, shape, and the like, of the user 110, the CI included in a sensor signal, to a virtual world processing apparatus.

In this instance, for example, the virtual world may be classified into a virtual environment and a virtual world object. In addition, the virtual world object may be classified into an avatar and a virtual object.

Depending on embodiments, the user 110 in the real world may include humans, animals, plants, inanimate objects, such as, articles, and even surrounding environment of the user 110; however, the present disclosure is not limited thereto.

Figure 2:
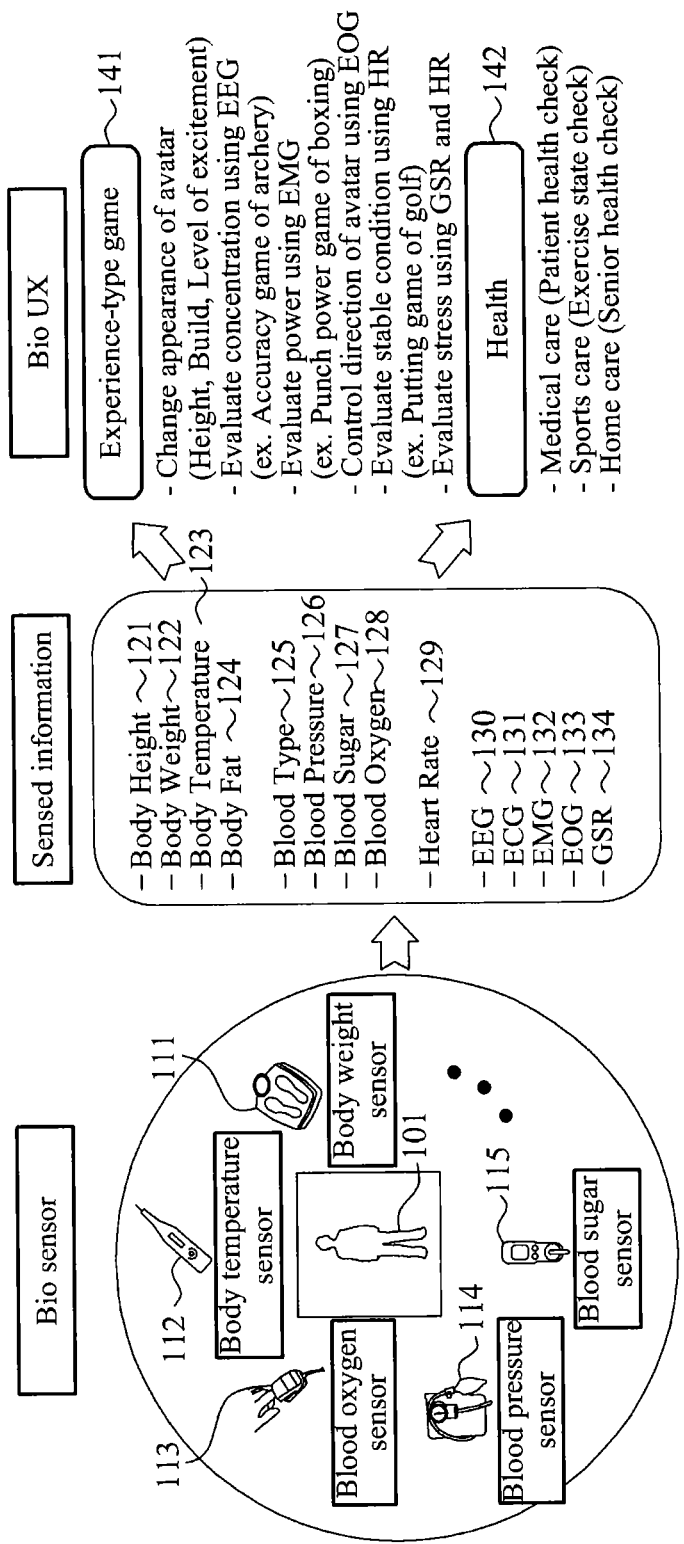
FIG. 2 illustrates a bio sensor, and sensed information collected by the bio sensor, according to example embodiments.

FIG. 2 illustrates a bio sensor and sensed information collected by the bio sensor, according to example embodiments.

Referring to FIG. 2, a virtual world processing apparatus may use bio sensors 111, 112, 113, 114, and 115 to collect information 121, 122, 123, 124, 125, 126, 127, 128, 129, 130, 131, 132, 133, and 134 about biometrics of a user 101, the user 101 being in a real world.

The bio sensors, for example, bio sensors 111 through 115, may collect information about biometrics of the user 101 in the real world. The bio sensors may include at least one of a body height sensor, a body weight sensor 111, a body temperature sensor 112, a body fat sensor, a blood type sensor, a blood pressure sensor 114, a blood sugar sensor 115, a blood oxygen sensor 113, a heart rate sensor, an electroencephalography (EEG) sensor, an electrocardiography (ECG) sensor, an electromyography (EMG) sensor, an electrooculography (EOG) sensor, a galvanic skin reflex (GSR) sensor, a bio sensor, and an electrograph sensor. The sensors listed above are exemplary, and thus, the present disclosure is not limited thereto.

The electrograph sensor may include at least one of the EEG sensor, the ECG sensor, the EMG sensor, the EOG sensor, and the GSR sensor.

The body height sensor may measure a body height 121 of the user 101 in the real world. The body weight sensor 111 may measure a body weight 122 of the user 101 in the real world. The body temperature sensor 112 may measure a body temperature 123 of the user 101 in the real world. The body fat sensor may measure a body fat 124 of the user 101 in the real world. The blood type sensor may measure a blood type 125 of the user 101 in the real world. The blood pressure sensor 114 may measure a blood pressure 126 of the user 101 in the real world. The blood sugar sensor 115 may measure an amount of glucose present in a blood of the user 101 in the real world, that is, a blood sugar 127. The blood oxygen sensor 113 may measure an amount of oxygen in the blood of the user 101 in the real world, that is, a blood oxygen 128. The heart rate sensor may measure a heart rate 129 of the user 101 in the real world. The EEG sensor may measure an EEG 130 of the user 101 in the real world. The ECG sensor may measure an ECG 131 of the user 101 in the real world. The EMG sensor may measure an EMG 132 of the user 101 in the real world. The EOG sensor may measure an EOG 133 of the user 101 in the real world. The GSR sensor may measure a GSR 134 of the user 101 in the real world. The electrograph sensor may measure an electrograph between a reference electrode and an active electrode. The sensors, and corresponding sensed information, listed above are exemplary, and thus, the present disclosure is not limited thereto.

The bio sensor may correspond to a sensor configured using a combination of at least two of the body height sensor, the body weight sensor 111, the body temperature sensor 112, the body fat sensor, the blood type sensor, the blood pressure sensor 114, the blood sugar sensor 115, the blood oxygen sensor 113, the heart rate sensor, the EEG sensor, the ECG sensor, the EMG sensor, the EOG sensor, the GSR sensor, and the electrograph sensor.

The virtual world processing apparatus may adapt the information collected with respect to the biometrics of the user 101 in the real world, based on capability of the bio sensor. In addition, the virtual world processing apparatus may control a bio user experience (Bio-UX) virtual world to which biometric information of the user 101 in the real world is to be applied, based on the adapted information.

According to example embodiments, the virtual world processing apparatus may control an experience-type game 141 that may be played in a virtual world, based on the adapted information.

For example, the virtual world processing apparatus may collect body weight information of the user 101 in the real world, using the body weight sensor 111, and may change an appearance of an avatar in the experience-type game 141, based on the collected body weight information.

The virtual world processing apparatus may collect EEG information of the user 101 in the real world, using the EEG sensor, and may adapt an ability with respect to a concentration in the experience-type game 141, for example, an archery game, based on the collected EEG information.

The virtual world processing apparatus may collect EMG information of the user 101 in the real world, using the EMG sensor, and may adapt an ability with respect to a power in the experience-type game 141, for example, an boxing game, based on the collected EMG information.

The virtual world processing apparatus may collect EOG information of the user 101 in the real world, using the EOG sensor, and may control a direction of an avatar in the experience-type game 141 based on the collected EOG information.

The virtual world processing apparatus may collect heart rate information of the user 101 in the real world, using the heart rate sensor, and may adapt an ability with respect to a stable condition in the experience-type game 141, for example, a golf game, based on the collected heart rate information.

According to example embodiments, the virtual world processing apparatus may collect a plurality of pieces of biometric information, using a plurality of bio sensors, and may control the experience-type game 141, based on the plurality of pieces of biometric information collected or sensed by the bio sensors.

For example, the virtual world processing apparatus may collect GSR information of the user 101 in the real world, using the GSR sensor, and may collect heart rate information of the user 101 using the heart rate sensor. Here, the GSR information may correspond to, for example, an emotional change of the user 101. The virtual world processing apparatus may adapt an ability with respect to a stress in the experience-type game 141, based on the collected GSR information and heart rate information.

According to example embodiments, the virtual world processing apparatus may determine a health 142 of the user 101 in the real world, based on adapted information.

For example, the virtual world processing apparatus may collect electrograph information between a reference electrode and an active electrode of the user 101, using the electrograph sensor, and may determine the health 142 of the user 101 in the real world, based on the collected electrograph information.

Accordingly, the virtual world processing apparatus may check a health of a patient, an exercise state, or a health of a senior, based on adapted information.

Figure 3:
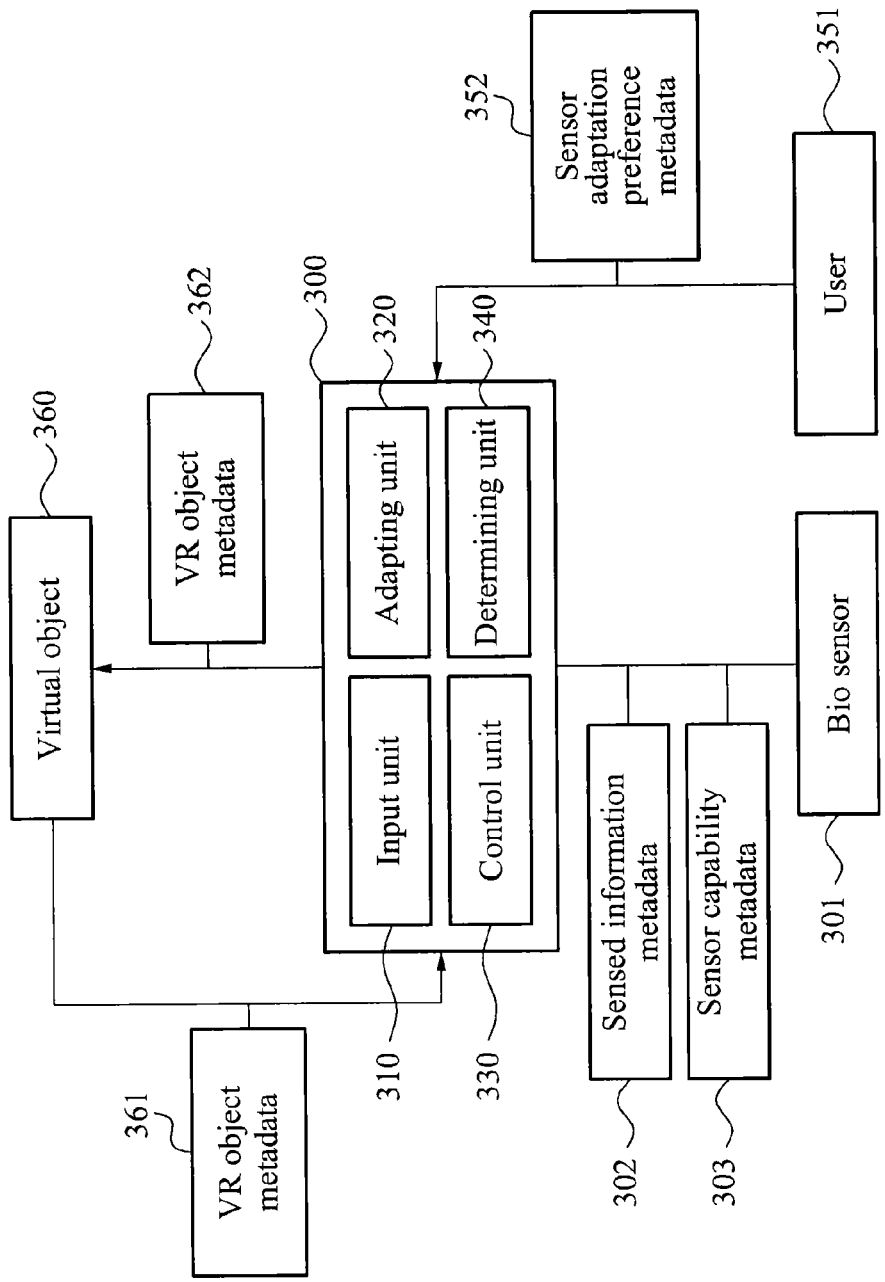
FIG. 3 illustrates a configuration of a virtual world processing apparatus, according to example embodiments.

FIG. 3 illustrates a configuration of a virtual world processing apparatus 300, according to example embodiments.

Referring to FIG. 3, a virtual world processing apparatus 300 that enables interoperability between a virtual world and a real world, or interoperability between virtual worlds may include at least an input unit 310 and an adapting unit 320.

The input unit 310 may receive an input of sensed information 302 collected by a bio sensor 301 with respect to biometrics of a user in the real world. The sensed information 302 will be described in detail later.

According to example embodiments, the input unit 310 may receive an input of a plurality of sensed information 302 from a plurality of bio sensors 301.

According to example embodiments, the input unit 310 may receive an input of virtual (VR) object metadata 361 indicating information with respect to a virtual object 360 in the virtual world. In addition, the input unit 310 may receive an input of a sensor adaptation preference metadata 352 for controlling the sensed information 302. The sensor adaptation preference 352 will be described in detail later.

The adapting unit 320 may adapt the sensed information 302, based on sensor capability metadata 303 associated with a capability of the bio sensor 301. The sensor capability metadata 303 will be described in detail later.

For example, when sensed information of 80 kilograms (kg) is collected as a result of sensing a body weight of a user 351 in the real world using a body weight sensor, the input unit 310 may receive an input of the sensed information of 80 kg. In this instance, when a maximum value (maxValue) of sensor capability with respect to the body weight sensor, corresponds to 70 kg, the adapting unit 320 may adapt the sensed information of 80 kg to 70 kg. In addition, the virtual world processing apparatus 300 may apply the sensed information of 70 kg adapted to the virtual world.

According to example embodiments, when the input unit 310 receives an input of the plurality of sensed information 302 from the plurality of bio sensors 301, the adapting unit 320 may adapt the plurality of sensed information 302, based on a plurality of sensor capabilities 303 respectively associated with the plurality of respective bio sensors 301.

According to example embodiments, the adapting unit 320 may adapt the VR object data 361 by applying the sensed information adapted, to the VR object data 361, thereby generating VR object data metadata 362.

According to example embodiments, the adapting unit 320 may adapt the sensed information 302, based on the sensor capability 303 and the sensor adaptation preference 352.

Depending on embodiments, the virtual world processing apparatus 300 may further include a control unit 330.

The control unit 330 may control an experience-type game played in the virtual world, based on the sensed information adapted by the adapting unit 320.

The control unit 330 may generate the VR object metadata 362 by applying the sensed information adapted, to the VR object metadata 361 indicating information about the virtual object 360 in the experience-type game, and may apply the generated VR object metadata 362 to the experience-type game, thereby controlling the experience-type game.

The virtual world processing apparatus 300 may further include a determining unit 340.

The determining unit 340 may determine a health of the user 351 in the real world, based on the sensed information adapted by the adapting unit 320.

The virtual world processing apparatus 300 may provide the user 351 with the health of the user 351 determined by the determining unit 340.

The sensor capability denotes information on capability of a sensor.

A sensor capability base type denotes a base type of the sensor capability. Depending on embodiments, the sensor capability base type may be a base abstract type of the metadata related to a sensor capability commonly applied to all types of sensors, as a portion of metadata types related to the sensor capability.

Hereinafter, the sensor capability and the sensor capability base type will be described in detail with reference to FIGS. 4 through 6.

Figure 4:
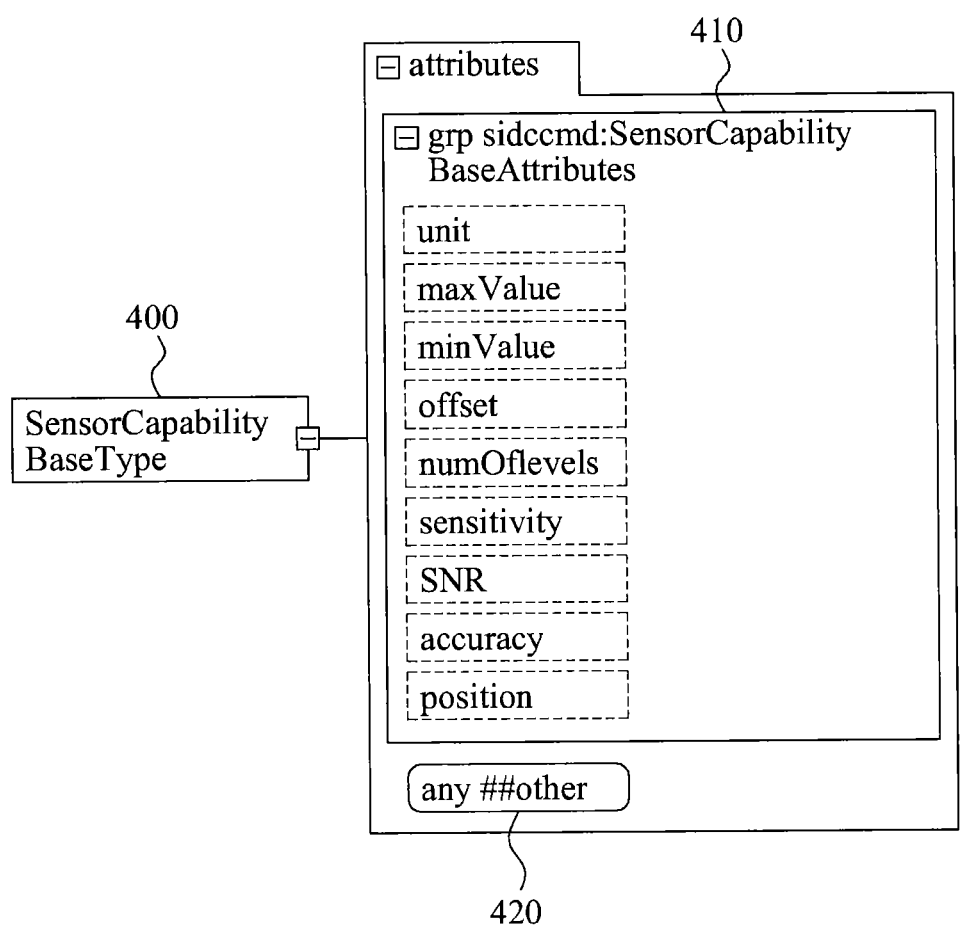
FIG. 4 illustrates a sensor capability base type, according to example embodiments.

FIG. 4 illustrates a sensor capability base type, according to example embodiments.

Referring to FIG. 4, a sensor capability base type 400 may include sensor capability base attributes 410 and any attributes 420.

The sensor capability base attributes 410 denotes a group of sensor capabilities that are basically included in the sensor capability base type 400.

The any attributes 420 denotes a group of additional sensor capabilities of a respective sensor. The any attributes 420 may correspond to unique additional sensor capabilities that may be applied to a predetermined sensor. The any attributes 420 may provide extensibility to include other attributes other than base attributes.

Figure 5:
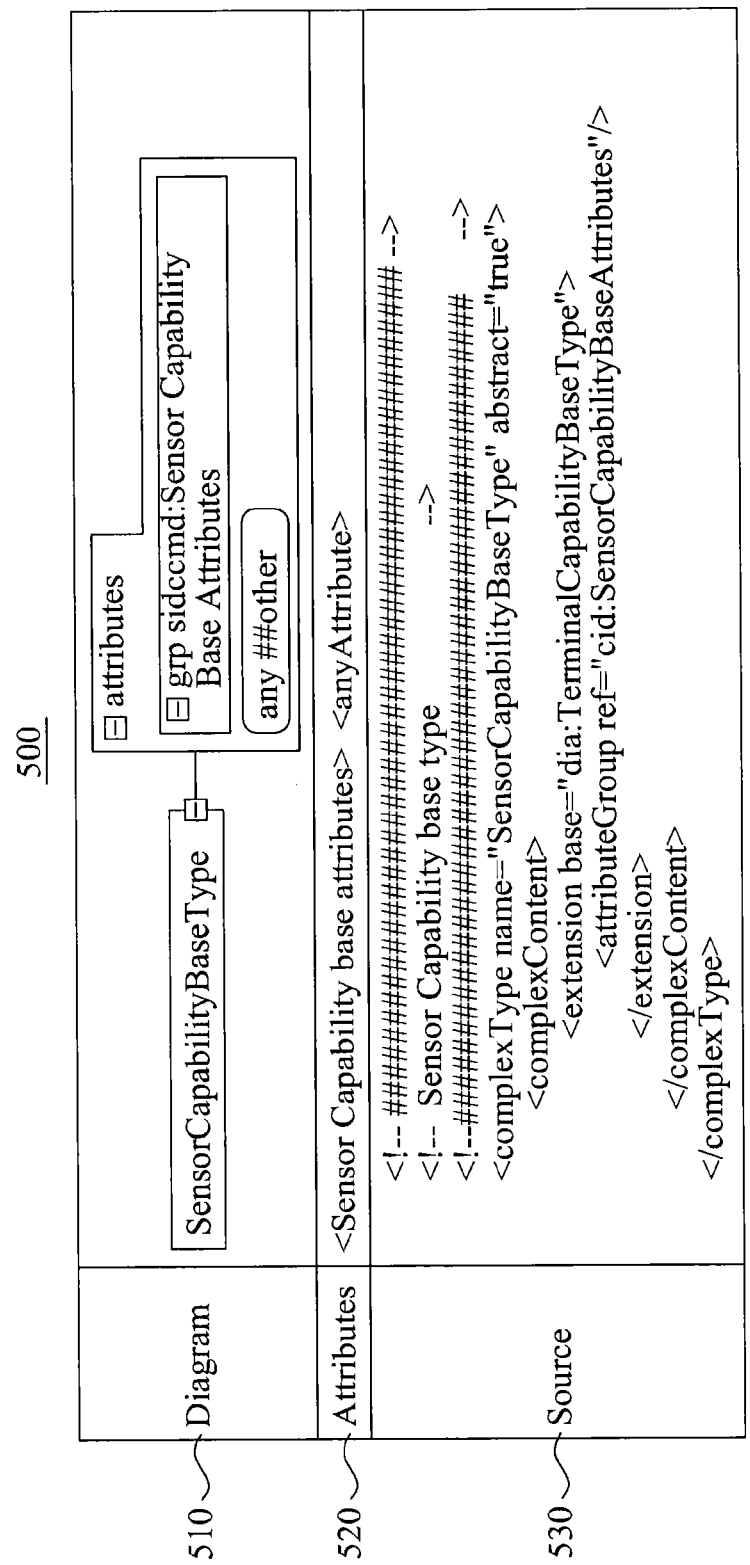
FIG. 5 illustrates a syntax of a sensor capability base type, according to example embodiments.

FIG. 5 illustrates a syntax 500 of a sensor capability base type, according to example embodiments.

Referring to FIG. 5, a syntax 500 of a sensor capability base type may include a diagram 510, attributes 520, and a source 530.

The diagram 510 may include a diagram of the sensor capability base type.

The attributes 520 may include sensor capability base attributes and any attributes.

The source 530 may include a program or code indicating the sensor capability base type, using Extensible Markup Language (XML), for example. However, the source 530 of FIG. 5 is provided only as an example, and example embodiments are not limited thereto.

FIG. 6 illustrates a syntax 600 of sensor capability base attributes, according to example embodiments.

Referring to FIG. 6, a syntax 600 of sensor capability base attributes may include a diagram 610, attributes 620, and a source 630.

The diagram 610 may include a diagram of the sensor capability base attributes.

The attributes 620 may include a unit 601, a maximum value (maxValue) 602, a minimum value (minValue) 603, an offset 604, a number of levels (numOflevels) 605, a sensitivity 606, a signal to noise ratio (SNR) 607, and an accuracy 608. These described attributes are exemplary, and thus, the present disclosure is not limited thereto.

The unit 601 denotes a unit of a value measured by a sensor. For example, when the sensor is a thermometer, the unit 601 may correspond to degree Celsius (° C.) and/or degree Fahrenheit (° F.). When the sensor is a speed sensor, the unit 601 may correspond to kilometers per hour (km/h) and meters per second (m/s).

The maxValue 602 denotes a maximum value that may be measured by the sensor, and the minValue 603 denotes a minimum value that may be measured by the sensor. For example, when the sensor is the thermometer, the maxValue 602 may correspond to 50° C., and the minValue 603 may correspond to 0° C. When the sensor is the same thermometer, the maxValue 602 and the minValue 603 may vary depending on purpose and performance of the sensor.

The offset 604 denotes a value to be added to a value measured by the sensor, in order to obtain an absolute value. For example, in a case in which the sensor is the speed sensor, when a user or an object in a real world is stationary, and a speed measures a value other than "0," the sensor may determine the offset 604 to be a value to be used to adapt the speed to "0." For example, when a speed measures −1 km/h with respect to a stationary automobile in the real world, the offset 604 may correspond to 1 km/h.

The numOflevels 605 denotes a number of values that may be measured by the sensor. That is, the numOflevels 605 may indicate a number of values that may be measured by the sensor, between a maximum value and a minimum value measured by the sensor. For example, in a case in which the sensor is the thermometer, the maximum value corresponds to 50° C., and the minimum value corresponds to 0° C., when the numOflevels 605 corresponds to 5, the sensor may measure five temperatures of 10° C., 20° C., 30° C., 40° C., and 50° C. As another non-limiting example, when a temperature in the real world corresponds to 20° C., the sensor may measure the temperature of 20° C. by performing a round-down operation. When the temperature in the real world corresponds to 27° C., the sensor may measure the temperature of 30° C. by performing a round-up operation.

The sensitivity 606 may denote a minimum input value to be used for the sensor to measure an output value. That is, the sensitivity 606 may indicate a minimum size of an input signal to be used to generate an output signal. For example, in a case in which the sensor is the thermometer, and the sensitivity 606 corresponds to 1° C., the sensor may fail to measure a temperature change less than 1° C., however, may measure a temperature change greater than or equal to 1° C. In particular, when the temperature increases from 15° C. to 15.5° C. in the real world, the sensor may still measure the temperature of 15° C.

The SNR 607 denotes a relative size of signal to noise of a value measured by the sensor. For example, in a case in which the sensor is a microphone, when a great deal of ambient noise is present in measuring a voice of a user in the real world, the SNR 607 of the sensor may correspond to a relatively a small value.

The accuracy 608 denotes an error of the sensor. That is, the accuracy 608 may indicate a degree of closeness of a measured quantity to an actual value. For example, when the sensor is the microphone, an error in measurement caused by a difference in propagation velocity of a voice according to temperature, humidity, and the like at a time of the measurement may correspond to the accuracy 608. In addition, the accuracy 608 of the sensor may be determined based on a statistical error rate of a value measured by the sensor in the past.

According to example embodiments, the attributes 620 may further include a location. The location denotes a location of the sensor. For example, when the sensor is the thermometer, the location of the sensor may correspond to a middle of an armpit of the user in the real world. The location may include a longitude, a latitude, a height from a ground, a direction from the ground, and the like.

The sensor capability base attributes, for example, the unit 601, the maxValue 602, the minValue 603, the offset 604, the numOflevels 605, the sensitivity 606, the SNR 607, the accuracy 608, and the location, may be arranged as shown in Table 1 below.

TABLE 1

| Name | Definition |
| --- | --- |
| unit 601 | denotes the unit of a value. |
| maxValue 602 | denotes the maximum value that the input device (sensor) can provide. The term will be different according to the individual device type. |
| minValue 603 | denotes the minimum value that the input device (sensor) can provide. The term will be different according to the individual device type. |
| offset 604 | denotes the number of value locations added to a base value in order to get to a specific absolute value. |
| numOflevels 605 | denotes the number of value levels that the device can provide in between the maximum value and the minimum value |
| sensitivity 606 | denotes the minimum magnitude of input signal required to produce a specified output signal. |
| SNR 607 | denotes the ratio of a signal power to the noise power corrupting the signal. |
| accuracy 608 | denotes the degree of closeness of a measured quantity to its actual value. |
| location | denotes the location of the device from the user's perspective according to the x-axis, y-axis, and z- axis. |

The source 630 may include a program or code indicating the sensor capability base attributes, using XML, for example.

A tag 631 expresses a definition of the maxValue 602 in XML. According to the tag 631, the maxValue 602 may have "float" type data, and may be optionally used.

A tag 632 expresses a definition of the minValue 603 in XML. According to the tag 632, the minValue 603 may have "float" type data, and may be optionally used.

A tag 633 expresses a definition of the numOflevels 605 in XML. According to the tag 633, the numOflevels 605 may have "nonNegativeInteger" type data, and may be optionally used.

However, the source 630 of FIG. 6 is provided only as an example, and example embodiments are not limited thereto.

Hereinafter, a sensor adaptation preference will be described in detail.

The sensor adaptation preference denotes information used to control a value received from a sensor. That is, the sensor adaptation preference may indicate preference information of a user with respect to a method of adapting sensed information collected by the sensor.

A sensor adaptation preference base type denotes a base type of controlled information of the user. Depending on example embodiments, the sensor adaptation preference base type may be a base abstract type of the metadata related to a sensor adaptation preference commonly applied to all types of sensors, as a portion of metadata types related to the sensor adaptation preference.

Hereinafter, the sensor adaptation preference and the sensor adaptation preference base type will be described in detail with reference to FIGS. 7 through 9.

Figure 7:
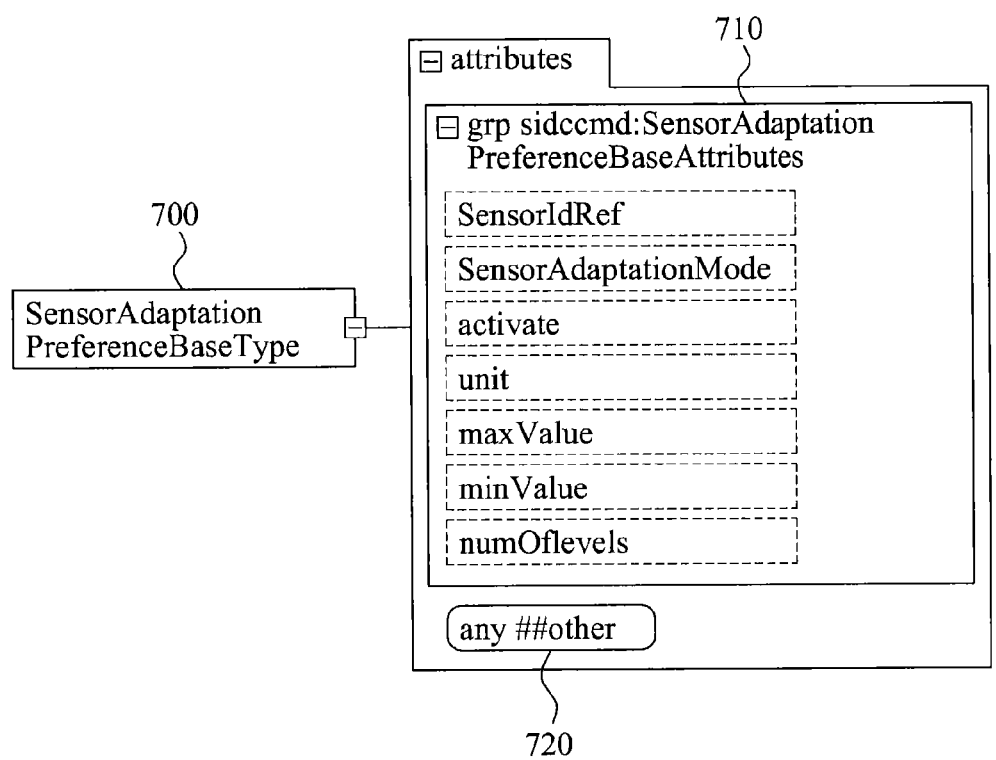
FIG. 7 illustrates a sensor adaptation preference base type, according to example embodiments.

FIG. 7 illustrates a sensor adaptation preference base type, according to example embodiments.

Referring to FIG. 7, a sensor adaptation preference base type 700 may include sensor adaptation preference base attributes 710 and any attributes 720.

The sensor adaptation preference base attributes 710 denotes a group of sensor adaptation preferences that are basically included in the sensor adaptation preference base type 700.

The any attributes 720 denotes a group of additional sensor adaptation preferences regarding a respective sensor. The any attributes 720 may correspond to unique additional sensor capabilities that may be applied to a predetermined sensor. The any attributes 720 may provide extensibility to include other attributes other than base attributes.

FIG. 8 illustrates a syntax 800 of a sensor adaptation preference base type, according to example embodiments.

Referring to FIG. 8, a syntax 800 of a sensor adaptation preference base type may include a diagram 810, attributes 820, and a source 830.

The diagram 810 may include a diagram of the sensor adaptation preference base type.

The attributes 820 may include sensor adaptation preference base attributes and any attributes.

The source 830 may include a program or code indicating the sensor adaptation preference base type, using XML, for example. However, the source 830 of FIG. 8 is provided only as an example, and example embodiments are not limited thereto. Additionally, the program of code of source 830 may be in a language other than XML, and thus, the present disclosure is not limited thereto.

FIG. 9 illustrates a syntax 900 of sensor adaptation preference base attributes, according to example embodiments.

Referring to FIG. 9, a syntax 900 of sensor adaptation preference base attributes may include a diagram 910, attributes 920, and a source 930.

The diagram 910 may include a diagram of the sensor adaptation preference base attributes.

The attributes 920 may include a sensor identification reference (sensorIdRef) 901, a sensor adaptation mode 902, an activate 903, a unit 904, a maxValue 905, a minValue 906, and a numOflevels 907.

The sensorIdRef 901 denotes information that references an identification (ID) of an individual sensor generating specific sensed information.

The sensor adaptation mode 902 denotes preference information of a user on an application method of a sensor. According to example embodiments, the sensor adaptation mode 902 may correspond to a sensor adaptation preference on an adaptation method for reflecting information in the virtual world by refining the information measured by the sensor, on a motion, a state, an intension, a shape, and the like, of the user in the real world. For example, a "strict" value may indicate a preference of the user to apply the sensed information of the real world to the virtual world directly. A "scalable" value may indicate a preference of the user to apply the sensed information of the real world to the virtual world, by changing the sensed information of the real world based on the preference of the user.

The activate 903 denotes information regarding whether a sensor is to be activated in the virtual world. For example, the activate 903 may correspond to a sensor adaptation preference to determine whether the sensor operates or not.

The unit 904 denotes a unit of a value to be used in the virtual world. For example, the unit 904 may correspond to a pixel. According to example embodiments, the unit 904 may correspond to a unit of a value corresponding to a value received from the sensor.

The maxValue 905 denotes a maximum value of a value to be used in the virtual world, and the minValue 906 denotes a minimum value of the value to be used in the virtual world. According to example embodiments, the maxValue 905 and the minValue 906 may correspond to a unit of a value corresponding to the value received from the sensor.

The numOflevels 907 denotes a number of values to be used in the virtual world. That is, the numOflevels 907 may indicate a number of values for dividing a number of operations between a maximum value and a minimum value of the value to be used in the virtual world.

The sensor adaptation preference base attributes, for example, the sensorIdRef 901, the sensor adaptation mode 902, the activate 903, the unit 904, the maxValue 905, the minValue 906, and the numOflevels 907, may be arranged as shown in Table 2 below. These attributes are exemplary, and thus, the present disclosure is not limited thereto.

TABLE 2

| Name | Definition |
| --- | --- |
| sensorIdRef 901 | refers the ID of an individual sensor that has generated the specific sensed information. |
| sensor adaptation mode 902 | denotes the user's preference on the adaptation method for the virtual world effect. |
| activate 903 | denotes whether the effect shall be activated. A value of true means effect shall be activated, and a value of false means the effect shall be deactivated. |
| unit 904 | denotes the unit of a value. |
| maxValue 905 | denotes the maximum desirable value of the effect in percentage according to the max scale defined within the semantics definition of the individual effects. |
| minValue 906 | denotes the minimum desirable value of the effect in percentage according to the min scale defined within the semantics definition of the individual effects. |
| numOflevels 907 | denotes the number of value levels that the device can provide in between the maximum value and the minimum value. |

The source 930 may include a program indicating the sensor adaptation preference base attributes, using XML, for example, however, the present disclosure is not limited thereto.

A tag 931 expresses a definition of the activate 903 in XML. According to the tag 931, the activate 903 may have "boolean" type data, and may be optionally used.

A tag 932 expresses a definition of the maxValue 905 in XML. According to the tag 932, the maxValue 905 may have "float" type data, and may be optionally used.

A tag 933 expresses a definition of the minValue 906 in XML. According to the tag 933, the minValue 906 may have "float" type data, and may be optionally used.

A tag 934 expresses a definition of the numOflevels 907 in XML. According to the tag 934, the numOflevels 907 may have a "nonNegativeInteger" type data, and may be optionally used.

However, the source 930 of FIG. 9 is provided only as an example, and example embodiments are not limited thereto.

Hereinafter, the sensed information will be described.

The sensed information may refer to information collected by a sensor in the real world.

According to example embodiments, the sensed information denotes a root element of metadata related to sensed information.

Hereinafter, the sensed information will be described in detail with reference to FIG. 10.

Figure 10:
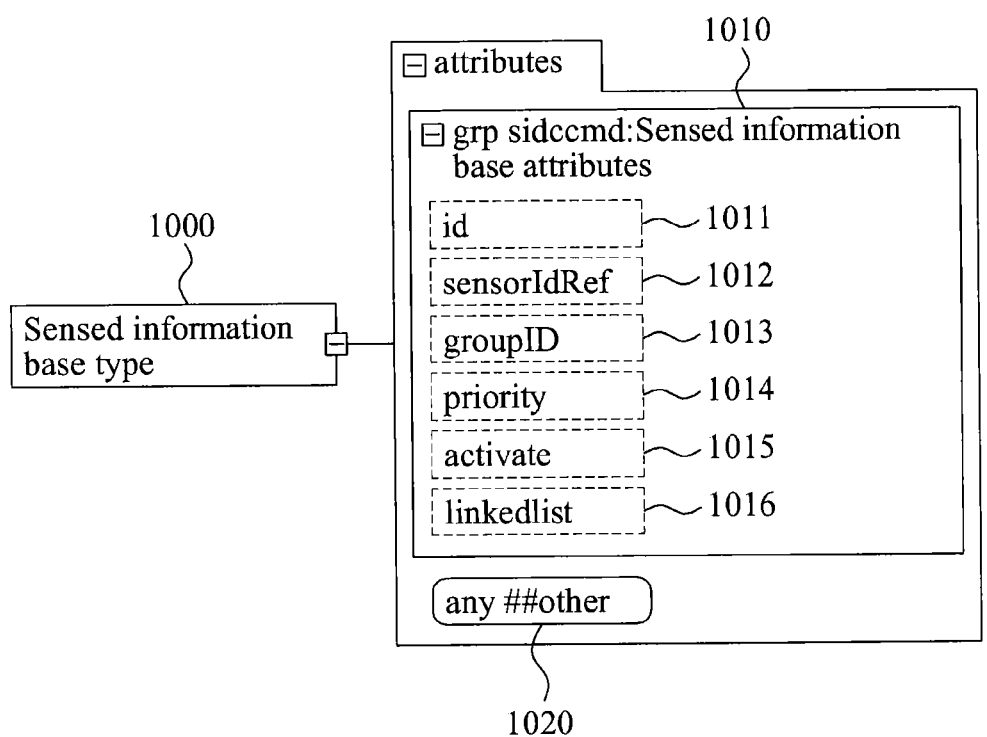
FIG. 10 illustrates a sensed information base type, according to example embodiments.

FIG. 10 illustrates a sensed information base type, according to example embodiments.

Referring to FIG. 10, a sensed information base type 1000 may include sensed information base attributes 1010 and any attributes 1020.

The sensed information base type 1000 may correspond to a topmost type of the base type that may inherit individual sensed information.

The sensed information base attributes 1010 denotes a group of attributes for commands.

The any attributes 1020 denotes a group of additional sensed information regarding a respective sensor. The any attributes 1020 may correspond to unique additional sensed information that may be applied to a predetermined sensor. The any attributes 1020 may provide extensibility to include other attributes other than base attributes.

Table 3 shows Source 1, as an example.

Source 1 may include a program or code indicating the sensed information base type, using XML, for example. However, Source 1 is provided only as an example, and example embodiments are not limited thereto.

TABLE 3

```
<!-- ################################################## -->
<!-- Sensed information base type                -->
<!-- ################################################## -->
<complexType name="SensedInfoBaseType" abstract="true">
    <sequence>
        <element name="Time stamp" type="mpegvct:Time
        stampType"/>
    </sequence>
    <attributeGroup ref="iidl:SensedInfoBaseAttributes"/>
</complexType>
```

The sensed information base attributes 1010 may include an ID 1011, a sensorIdRef 1012, a group ID (groupID) 1013, a priority 1014, an activate 1015, and a linked list (linkedlist) 1016. These described base attributes are exemplary, and thus, the present disclosure is not limited thereto.

The ID 1011 may denote ID information to be used to identify an individual identity of sensed information collected by a respective sensor.

The sensorIdRef 1012 may denote information that references the respective sensor. That is, the sensorIdRef 1012 may refer to information that references an ID of the sensor that generates information included in specific sensed information.

The groupID 1013 may denote information to be used to identify an individual identity of a multi-sensor group including the sensor. That is, the groupID 1013 may refer to ID information to be used to identify an individual identity of a multi-sensor structure including a predetermined sensor.

The priority 1014 denotes priority information of sensed information with respect to another piece of sensed information that shares a same point in a time at which the sensed information is adapted. For example, a value of "1" may indicate a highest priority. In this instance, the greater the value is, the lower the priority.

A default value of the priority 1014 may correspond to "1." When at least one pieces of sensed information having an identical priority is provided, a sequence for processing the sensed information may be determined by an adaptation engine.

The priority 1014 may be used to apply the sensed information to virtual world object capabilities based on adaptation VR capabilities. The virtual world object capabilities may be defined in a group of sensors. For example, the adaptation VR may process individual sensed information in the group of the sensors in a descending order of the priority 1014, due to limited capability of the adaptation VR. That is, sensed information having a relatively low priority 1014 may be lost.

The activate 1015 denotes information to be used to determine whether the sensor operates. A value of "true" may indicate that the sensor is to be activated, and a value of "false" may indicate that the sensor is to be deactivated.

The linkedlist 1016 denotes link information to be used to group multiple sensors. For example, the linkedlist 1016 may refer to information on a multi-sensor group, to be used to group sensors using a method of containing reference information on an ID of a neighboring sensor.

According to example embodiments, the sensed information base attributes 1010 may further include a value, a timestamp, and a life span.

The value denotes a measured value. The value may correspond to a value received from a sensor.

The timestamp denotes time information when the sensor performs sensing.

The life span denotes information on a term of validity for sensor commands. For example, the life span may correspond to a unit of a second.

The sensed information base attributes may be arranged as shown in Table 4 below. These base attributes are exemplary, and thus, the present disclosure is not limited thereto.

TABLE 4

| Name | Definition |
| --- | --- |
| ID 1011 | denotes an individual identity of a sensor. |
| sensorIdRef 1012 | references a sensor that has generated the information included in this specific sensed information. |
| groupID 1013 | denotes an identifier for a group multi-sensor structure to which this specific sensor belongs. |
| priority 1014 | describes the priority for sensed information with respect to other sensed information in the same group of sensors sharing the same point in time when the sensed information becomes adapted. A value of one indicates the highest priority and larger values indicate lower priorities. |
| activate 1015 | denotes whether the effect shall be activated. A value of true means the effect shall be activated, and a value of false means the effect shall be deactivated. |
| value | denotes the value of the effect in a percentage according to the max scale defined within the semantics definition of the individual effects. |
| linkedlist 1016 | denotes a grouping sensor structure that consists of a group of sensors such that in each record there is a field that contains a reference (ID) to the next sensor. |
| timestamp | denotes time information when the sensor performs sensing. |
| life span | denotes information on the term of validity for sensor commands. The term of validity may be indicated based on the timestamp. The life span may correspond to second units. |

Hereinafter, sensed information with respect to detailed examples of a sensor will be described.

Table 5 shows Source 2, as an example.

Source 2 shows sensed information with respect to a body height sensor, using XML, for example. However, a program source of Source 2 is provided only as an example, and example embodiments are not limited thereto.

TABLE 5

```
<!--################################### -->
<!--Definition of Body Height Sensor type -->
<!--################################### -->
<complexType name="BodyHeightSensorType">
    <complexContent>
        <extension base="iidl:SensedInfoBaseType">
            <attribute name="value" type="float" use="required"/>
            <attribute name="unit" type="mpegvct:unitType" use="optional"/>
        </extension>
    </complexContent>
</complexType>
```

A body height sensor type may correspond to a tool to describe the sensed information with respect to the body height sensor.

The body height sensor type may include at least one of attributes of a timestamp, a unit, and a value.

The timestamp denotes information about a sensing time of the body height sensor.

The unit denotes information about a unit of the sensed information of the body height sensor. For example, a unit of the sensed information of the body height sensor may be inches or centimeters.

The value denotes information about a value sensed by the body height sensor. For example, the value may be sensed in units of centimeters (cm).

Table 6 shows Example 1.

Example 1 shows an example of the body height sensor type. However, Example 1 is provided as only an example of the body height sensor type, and example embodiments are not limited thereto.

TABLE 6

```
<iidl:SensedInfo xsi:type="iidl:BodyHeightSensorType" id="BHS001"
sensorIdRef="BHSID001" activate="true" timestamp="100.0"
value="170.5" />
```

Referring to Example 1, the sensed information measured by the body height sensor may correspond to a value of 170.5 cm.

Table 7 shows a binary representation syntax of the body height sensor type, according to example embodiments.

TABLE 7

| BodyHeightSensorType{ | Number of bits | Mnemonic |
|---|---|---|
| unitFlag | 1 | bslbf |
| SensedInfoBaseType | See above | SensedInfoBaseType |
| value | 32 | fsfb |
| If (unitFlag == 1){ | | |
|    unit | | unitType |
| } | | |
| } | | |

Table 8 shows additional semantics for the binary representation of the body height sensor type.

TABLE 8

| Name | Definition |
|---|---|
| unitFlag | This field, which is only present in the binary representation, signals that a unit other than a default unit is being used. A value of "1" means that the unit being used is specified in unit attributes, and "0" means that the default unit is being used. |

As described in Table 8, the binary representation may indicate at least one flag as a data field. That is, using the binary representation, the sensed information may include the at least one flag.

Each of the at least one flag may indicate whether corresponding sensed information includes a predetermined field. When a value of a predetermined flag corresponds to "0," a predetermined field corresponding to the predetermined flag may fail to be included in the sensed information. Accordingly, using the flag, an amount of data corresponding to the sensed information may be limited.

Table 9 shows Source 3, as an example.

Source 3 shows sensed information with respect to a body weight sensor, using XML, for example. However, a program source of Source 3 is provided only as an example, and example embodiments are not limited thereto.

TABLE 9

```
<!--################################### -->
<!--Definition of Body Weight Sensor type -->
<!--################################### -->
<complexType name="BodyWeightSensorType">
    <complexContent>
        <extension base="iidl:SensedInfoBaseType">
            <attribute name="value" type="float" use=" required"/>
            <attribute name="unit" type="mpegvct:unitType" use="optional"/>
        </extension>
    </complexContent>
</complexType>
```

A body weight sensor type may correspond to a tool to describe sensed information with respect to the body weight sensor.

The body weight sensor type may include at least one of attributes of a timestamp, a unit, and a value.

The timestamp denotes information about a sensing time of the body weight sensor.

The unit denotes information about a unit of the sensed information of the body weight sensor. For example, a unit of sensed information of the body weight sensor may be in kilograms (kg).

The value denotes information about a value sensed by the body weight sensor. For example, the value may be sensed in units of kg.

Table 10 shows Example 2.

TABLE 10

```
<iidl:SensedInfo xsi:type="iidl:BodyWeightSensorType" id="BWS001"
sensorIdRef="BWSID001" activate="true" timestamp="100.0"
value="65.4" />
```

Example 2 shows an example of the body weight sensor type. However, Example 2 is provided as only an example of the body weight sensor type, and example embodiments are not limited thereto.

Referring to Example 2, the sensed information measured by the body weight sensor may correspond to a value of 65.4 kg.

Table 11 shows a binary representation syntax of the body weight sensor type.

TABLE 11

| BodyWeightSensorType{ | Number of bits | Mnemonic |
|---|---|---|
| unitFlag | 1 | bslbf |
| SensedInfoBaseType value | See above 32 | SensedInfoBaseType fsfb |
| If (unitFlag == 1){ | | |
|   unit | | unitType |
| } | | |
| } | | |

Table 12 shows additional semantics for the binary representation of the body weight sensor type, according to example embodiments.

TABLE 12

| Name | Definition |
|---|---|
| unitFlag | This field, which is only present in the binary representation, signals that a unit other than a default unit is being used. A value of "1" means that the unit being used is specified in unit attributes, and "0" means that the default unit is being used. |

Table 13 shows Source 4, as an example.

TABLE 13

```
<!--#####################################-->
<!--Definition of Body Temperature Sensor type -->
<!--#####################################-->
<complexType name="BodyTemperatureSensorType">
    <complexContent>
        <extension base="iidl:SensedInfoBaseType">
            <attribute name="value" type="float" use="required"/>
            <attribute name="unit" type="mpegvct:unitType" use="optional"/>
            <attribute name="location" type="nonNegativeInteger" use="optional"/>
        </extension>
    </complexContent>
</complexType>
```

Source 4 shows sensed information with respect to a body temperature sensor, using XML, for example. However, a program source of Source 4 is provided only as an example, and example embodiments are not limited thereto.

A body temperature sensor type may correspond to a tool to describe sensed information with respect to the body temperature sensor.

The body temperature sensor type may include at least one of attributes of a timestamp, a unit, a value, and a location.

The timestamp denotes information about a sensing time of the body temperature sensor.

The unit denotes information about a unit of the sensed information of the body temperature sensor. For example, a unit of the sensed information of the body temperature sensor may be in degrees Celsius (° C.).

The value denotes information about a value sensed by the body temperature sensor. For example, the value may be sensed in units of ° C.

The location denotes information about a location at which the body temperature sensor performs sensing. For example, the location may include a general body temperature, an axillary, an ear, a finger, a gastro-intestinal tract, a mouth, a rectum, a toe, and a tympanum, however, the present disclosure is not limited thereto.

Table 14 shows Example 3.

TABLE 14

```
<iidl:SensedInfo xsi:type="iidl:BodyTemperatureSensorType"
id="BTS001" sensorIdRef="BTSID001" activate="true"
timestamp="100.0" value="36.5" location="6"/>
```

Example 3 shows an example of the body temperature sensor type. However, Example 3 is provided as only an example of the body temperature sensor type, and example embodiments are not limited thereto.

Referring to Example 3, the sensed information measured by the body temperature sensor may correspond to a value of 36.5° C.

Table 15 shows a binary representation syntax of the body temperature sensor type.

TABLE 15

| BodyTemperatureSensorType{ | Number of bits | Mnemonic |
|---|---|---|
| unitFlag | 1 | bslbf |
| locationFlag | 1 | bslbf |
| SensedInfoBaseType value | See above 32 | SensedInfoBaseType fsfb |
| If (unitFlag == 1){ | | |
|   unit | | unitType |
| } | | |
| if (locationFlag == 1){ | | |
|   location | 4 | bslbf |
| } | | |
| } | | |

Table 16 shows additional semantics for the binary representation of the body temperature sensor type, according to example embodiments.

TABLE 16

| Name | Definition |
|---|---|
| unitFlag | This field, which is only present in the binary representation, signals that a unit other than a default unit is being used. A value of "1" means that the unit being used is specified in unit attributes, and "0" means that the default unit is being used. |
| locationFlag | This field, which is only present in the binary representation, signals the use of a body location type. A value of "1" means the use of the body location type, and "0" means the use of a default location. |
| location | This field describes position information regarding a location in which the sensor is sensed. |

Table 17 below shows a binary representation of the location field and position information, according to example embodiments.

TABLE 17

| Binary representation (4 bits) | Position information |
|---|---|
| 0 | Reserved |
| 1 | General body temperature |
| 2 | Axillary (armpit) |
| 3 | Ear (usually earlobe) |
| 4 | Finger |
| 5 | Gastro-intestinal tract |
| 6 | Mouth |
| 7 | Rectum |
| 8 | Toe |

TABLE 17-continued

| Binary representation (4 bits) | Position information |
|---|---|
| 9 | Tympanum (ear drum) |
| 10-15 | reserved |

Table 18 shows Source 5, as an example.

TABLE 18

```
<!--######################################-->
<!--Definition of Body Fat Sensor type -->
<!--######################################-->
<complexType name="BodyFatSensorType">
    <complexContent>
        <extension base="iidl:SensedInfoBaseType">
            <attribute name="value" type="float" use=" required "/>
            <attribute name="unit" type="mpegvct:unitType" use="optional"/>
        </extension>
    </complexContent>
</complexType>
```

Source 5 shows sensed information with respect to a body fat sensor, using XML, for example. However, a program source of Source 5 is provided only as an example, and example embodiments are not limited thereto.

A body fat sensor type may correspond to a tool to describe sensed information with respect to the body fat sensor.

The body fat sensor type may include at least one of attributes of a timestamp, a unit, and a value.

The timestamp denotes information about a sensing time of the body fat sensor.

The unit denotes information about a unit of the sensed information of the body fat sensor.

The value denotes information about a value sensed by the body fat sensor. For example, the value may be sensed in units of a percentage (%).

Table 19 shows Example 4.

TABLE 19

```
<iidl:SensedInfo xsi:type="iidl:BodyFatSensorType" id="BFS001"
sensorIdRef="BFSID001" activate="true" timestamp="100.0"
value="75" />
```

Example 4 shows an example of the body fat sensor type. However, Example 4 is provided as only an example of the body fat sensor type, and example embodiments are not limited thereto.

Referring to Example 4, the sensed information measured by the body fat sensor may correspond to a value of 75%.

Table 20 shows a binary representation syntax of the body fat sensor type.

TABLE 20

| BodyFatSensorType{ | Number of bits | Mnemonic |
|---|---|---|
| unitFlag | 1 | bslbf |
| SensedInfoBaseType | See above | SensedInfoBaseType |
| value | 32 | fsfb |
| If (unitFlag == 1){ | | |
|    unit | | unitType |
| } | | |
| } | | |

Table 21 shows additional semantics for the binary representation of the body fat sensor type, accordingly to example embodiments.

TABLE 21

| Name | Definition |
|---|---|
| unitFlag | This field, which is only present in the binary representation, signals that a unit other than a default unit is being used. A value of "1" means that the unit being used is specified in unit attributes, and "0" means that the default unit is being used. |

Table 22 shows Source 6, as an example.

TABLE 22

```
<!--######################################-->
<!--Definition of Blood Type Sensor type -->
<!--######################################-->
<complexType name="BloodTypeSensorType">
<complexContent>
<extension base="iidl:SensedInfoBaseType">
<sequence>
<element name="ABOType">
<simpleType>
<restriction base="string">
<enumeration value="A"/>
<enumeration value="B"/>
<enumeration value="AB"/>
<enumeration value="O"/>
</restriction>
</simpleType>
</element>
<element name="RhType">
<simpleType>
<restriction base="string">
<enumeration value="+"/>
<enumeration value="-"/>
</restriction>
</simpleType>
</element>
</sequence>
</extension>
</complexContent>
</complexType>
```

Source 6 shows sensed information with respect to a blood type sensor, using XML, for example. However, a program source of Source 6 is provided only as an example, and example embodiments are not limited thereto.

A blood type sensor type may correspond to a tool to describe sensed information with respect to the blood type sensor.

The blood type sensor type may include at least one of attributes of an ABO type and an Rh type.

The ABO type denotes information about ABO blood types sensed by the blood type sensor. For example, the ABO blood types may include A, B, AB, and O.

The Rh type denotes information about Rh blood types sensed by the blood type sensor. For example, the Rh types may include Rh positive (+) and Rh negative (−).

Table 23 shows Example 5.

TABLE 23

```
<iidl:SensedInfo xsi:type="iidl:BloodTypeSensorType" id="BTYS001"
sensorIdRef="BTYSID001" activate="true" timestamp="100.0"
ABOType="A" RhType="+" />
```

Example 5 shows an example of the blood type sensor type. However, Example 5 is provided as only an example of the blood type sensor type, and example embodiments are not limited thereto.

Referring to Example 5, the sensed information measured by the blood type sensor may correspond to an ABO type of A, and an Rh type of Rh+.

Table 24 shows a binary representation syntax of the blood type sensor type, according to example embodiments.

TABLE 24

| BloodTypeSensorType | Number of bits | Mnemonic |
|---|---|---|
| SensedInfoBaseType | See above | SensedInfoBaseType |
| ABOType | 3 | bslbf |
| RhType | 1 | bslbf |
| } | | |

Table 25 shows additional semantics for the binary representation of the blood type sensor type, accordingly to example embodiments.

TABLE 25

| Name | Definition |
|---|---|
| ABOType | describes a sensed value of ABO blood types, for example, A, B, AB, and O. Table 26 specifies binary representations of respective types. |
| RHType | describes a sensed value of Rh blood types, for example, Rh positive (+) and Rh negative (1). (0: Rh positive (+), 1: Rh negative (−)) |

Table 26 shows a binary representation and types of the ABOType field, according to example embodiments.

TABLE 26

| Binary representation (3 bits) | Type |
|---|---|
| 0 | A |
| 1 | B |
| 2 | AB |
| 3 | O |
| 4-7 | reserved |

Table 27 shows Source 7, as an example.

TABLE 27

```
<!--######################################## -->
<!--Definition of Blood Pressure Sensor type -->
<!--######################################## -->
<complexType name="BloofPressureSensorType">
    <complexContent>
        <extension base="iidl:SensedInfoBaseType">
            <attribute name="SystolicBP" type="float" use=" required "/>
<attribute name="DiastolicBP" type="float" use=" required "/>
<attribute name="MAP" type="float" use="optional"/>
            <attribute name="unit" type="mpegvct:unitType" use="optional"/>
        </extension>
    </complexContent>
</complexType>
```

Source 7 shows sensed information with respect to a blood pressure sensor, using XML, for example. However, a program source of Source 7 is provided only as an example, and example embodiments are not limited thereto.

A blood pressure sensor type may correspond to a tool to describe sensed information with respect to the blood pressure sensor.

The blood pressure sensor type may include at least one of attributes of a timestamp, a unit, a systolic blood pressure (systolicBP), a diastolic blood pressure (diastolic BP), and a mean arterial pressure (MAP).

The timestamp denotes information about a sensing time of the blood pressure sensor.

The unit denotes information about a unit of the sensed information of the blood pressure sensor.

The systolicBP denotes information about a systolic blood pressure sensed by the blood pressure sensor.

The diastolicBP denotes information about a diastolic blood pressure sensed by the blood pressure sensor.

The MAP denotes information about a mean arterial pressure sensed by the blood pressure sensor.

Table 28 shows Example 6.

TABLE 28

<iidl:SensedInfo xsi:type="iidl:BloodPressureSensorType" id="BPS001" sensorIdRef="BPSID001" activate="true" timestamp="100.0" SystolicBP="121" DiastolicBP="83" MAP="100" />

Example 6 shows an example of the blood pressure sensor type. However, Example 6 is provided as only an example of the blood pressure sensor type, and example embodiments are not limited thereto.

Referring to Example 6, the sensed information measured by the blood pressure sensor may correspond to a systolicBP of 121, a diastolicBP of 83, and an MAP of 100.

Table 29 shows a binary representation syntax of the blood pressure sensor type, according to example embodiments.

TABLE 29

| BloodPressureSensorType{ | Number of bits | Mnemonic |
|---|---|---|
| unitFlag | 1 | bslbf |
| systolicBPFlag | 1 | bslbf |
| diastolicBPFlag | 1 | bslbf |
| MAPFlag | 1 | bslbf |
| SensedInfoBaseType | See above | SensedInfoBaseType |
| if (systolicBPFlag == 1) { | | |
|   systolicBP | 32 | fsfb |
| } | | |
| if (diastolicBPFlag == 1) { | | |
|   diastolicBP | 32 | fsfb |
| } | | |
| if (MAPFlag == 1) { | | |
|   MAP | 32 | fsfb |
| } | | |
| if (unitFlag == 1){ | | |
|   unit | | unitType |
| } | | |
| } | | |

Table 30 shows additional semantics for the binary representation of the blood pressure sensor type, according to example embodiments.

TABLE 30

| Name | Definition |
|---|---|
| unitFlag | This field, which is only present in the binary representation, signals that a unit other than a default unit is being used. A value of "1" means that the unit being used is specified in unit attributes, and "0" means that the default unit is being used. |
| systolicBPFlag | This field, which is only present in the binary representation, signals whether a value of systolicBP is present. A value of "1" means the value of systolicBP is present, and "0" means the value of systolicBP is absent. |
| diastolicBPFlag | This field, which is only present in the binary representation, signals whether a value of diastolicBP is present. A value of "1" means the value of diastolicBP is present, and "0" means the value of diastolicBP is absent. |

TABLE 30-continued

| Name | Definition |
| --- | --- |
| MAPFlag | This field, which is only present in the binary representation, signals whether a value of MAP is present. A value of "1" means the value of MAP is present, and "0" means the value of MAP is absent. |

Table 31 shows Source 8, as an example.

TABLE 31

```
<!--###################################### -->
<!--Definition of Blood Sugar Sensor type -->
<!--###################################### -->
<complexType name="BloodSugarSensorType">
    <complexContent>
        <extension base="iidl:SensedInfoBaseType">
            <attribute name="value" type="float" use=" required "/>
            <attribute name="unit" type="mpegvct:unitType" use="optional"/>
        </extension>
    </complexContent>
</complexType>
```

Source 8 shows sensed information with respect to a blood sugar sensor, using XML, for example. However, a program source of Source 8 is provided only as an example, and example embodiments are not limited thereto.

A blood sugar sensor type may correspond to a tool to describe sensed information with respect to the blood sugar sensor.

The blood sugar sensor type may include at least one of attributes of a timestamp, a unit, and a value.

The timestamp denotes information about a sensing time of the blood sugar sensor.

The unit denotes information about a unit of the sensed information of the blood sugar sensor.

The value denotes information about a value sensed by the blood sugar sensor. For example, the value may be sensed in units of milligrams per deciliter (mg/dL).

Table 32 shows Example 7.

TABLE 32

```
<iidl:SensedInfo xsi:type="iidl:BloodSugarSensorType" id="BSS001"
sensorIdRef="BSSID001" activate="true" timestamp="100.0"
value="115" />
```

Example 7 shows an example of the blood sugar sensor type. However, Example 7 is provided as only an example of the blood sugar sensor type, and example embodiments are not limited thereto.

Referring to Example 7, the sensed information measured by the blood sugar sensor may correspond to a value of 115 mg/dL.

Table 33 shows a binary representation syntax of the blood sugar sensor type, accordingly to example embodiments.

TABLE 33

| BloodSugarSensorType{ | Number of bits | Mnemonic |
| --- | --- | --- |
| unitFlag | 1 | bslbf |
| SensedInfoBaseType | See above | SensedInfoBaseType |
| value | 32 | fsfb |
| If (unitFlag == 1){ | | |
|     unit | | unitType |
| } | | |
| } | | |

Table 34 shows additional semantics for the binary representation of the blood sugar sensor type, according to example embodiments.

TABLE 34

| Name | Definition |
| --- | --- |
| unitFlag | This field, which is only present in the binary representation, signals that a unit other than a default unit is being used. A value of "1" means that the unit being used is specified in unit attributes, and "0" means that the default unit is being used. |

Table 35 shows a binary representation syntax of a blood oxygen sensor type, according to example embodiments.

TABLE 35

| BloodOxygenSensorType{ | Number of bits | Mnemonic |
| --- | --- | --- |
| unitFlag | 1 | bslbf |
| SensedInfoBaseType | See above | SensedInfoBaseType |
| value | 32 | fsfb |
| If (unitFlag == 1){ | | |
|     Unit | | unitType |
| } | | |
| } | | |

Table 36 shows additional semantics for the binary representation of the blood oxygen sensor type, according to example embodiments.

TABLE 36

| Name | Definition |
| --- | --- |
| unitFlag | This field, which is only present in the binary representation, signals that a unit other than a default unit is being used. A value of "1" means that the unit being used is specified in unit attributes, and "0" means that the default unit is being used. |

Table 37 shows Source 9, as an example.

TABLE 37

```
<!--###################################### -->
<!--Definition of Heart Rate Sensor type -->
<!--###################################### -->
<complexType name="HeartRateSensorType">
    <complexContent>
        <extension base="iidl:SensedInfoBaseType">
            <attribute name="value" type="float" use=" required "/>
            <attribute name="unit" type="mpegvct:unitType" use="optional"/>
        </extension>
    </complexContent>
</complexType>
```

Source 9 shows sensed information with respect to a heart rate sensor, using XML, for example. However, a program source of Source 9 is provided only as an example, and example embodiments are not limited thereto.

A heart rate sensor type may correspond to a tool to describe sensed information with respect to the heart rate sensor.

The heart rate sensor type may include at least one of attributes of a timestamp, a unit, and a value.

The timestamp denotes information about a sensing time of the heart rate sensor.

The unit denotes information about a unit of the sensed information of the heart rate sensor.

The value denotes information about a value sensed by the heart rate sensor. For example, the value may be sensed in units of beats per minute (bpm).

Table 38 shows Example 8.

TABLE 38

<iidl:SensedInfo xsi:type="iidl:HeartRateSensorType" id="HRS001" sensorIdRef="HRSID001" activate="true" timestamp="100.0" value="65" />

Example 8 shows an example of the heart rate sensor type. However, Example 8 is provided as only an example of the heart rate sensor type, and example embodiments are not limited thereto.

Referring to Example 8, the sensed information measured by the heart rate sensor may correspond to a value of 65 bpm.

Table 39 shows a binary representation syntax of the heart rate sensor type, according to example embodiments.

TABLE 39

| HearRateSensorType{ | Number of bits | Mnemonic |
|---|---|---|
| unitFlag | 1 | bslbf |
| SensedInfoBaseType | See above | SensedInfoBaseType |
| value | 32 | fsfb |
| If (unitFlag == 1){ | | |
| unit | | unitType |
| } | | |
| } | | |

Table 40 below shows additional semantics for the binary representation of the heart rate sensor type, according to example embodiments.

TABLE 40

| Name | Definition |
|---|---|
| unitFlag | This field, which is only present in the binary representation, signals that a unit other than a default unit is being used. A value of "1" means that the unit being used is specified in unit attributes, and "0" means that the default unit is being used. |

Table 41 shows Source 10, as an example.

TABLE 41

<!--######################################## -->
<!--Definition of EEG Sensor type -->
<!--######################################## -->
<complexType name="EEGSensorType">
    <complexContent>
        <extension base="iidl:SensedInfoBaseType">
            <attribute name="array_value" type=" mpeg7:FloatMatrixType" use=" required "/>
                <attribute name="unit" type="mpegvct:unitType" use="optional"/>
        </extension>
    </complexContent>
</complexType>

Source 10 shows sensed information with respect to an EEG sensor, using XML, for example. However, a program source of Source 10 is provided only as an example, and example embodiments are not limited thereto.

An EEG sensor type may correspond to a tool to describe sensed information with respect to the EEG sensor.

The EEG sensor type may include at least one of attributes of a timestamp, a unit, and an array value.

The timestamp denotes information about a sensing time of the EEG sensor.

The unit denotes information about a unit of the sensed information of the EEG sensor.

The array value denotes information about a value sensed by the EEG sensor. For example, the array value may be sensed in units of microvolts (μV).

Table 42 shows Example 9.

TABLE 42

<iidl:SensedInfo xsi:type="iidl:EEGSensorType" id="EEGS001" sensorIdRef="EEGSID001" activate="true" timestamp="100.0">
    <iidl:array_value n1:dim="12">10.3 9.8 10.1 5.3 1.0 4.5 10.7 9.8 11.2 7.7 12.2 5.5</iidl:array_value>
</iidl:SensedInfo>

Example 9 shows an example of the EEG sensor type. However, Example 9 is provided as only an example of the EEG sensor type, and example embodiments are not limited thereto.

Table 43 shows a binary representation syntax of the EEG sensor type, according to example embodiments.

TABLE 43

| EEGSensorType{ | Number of bits | Mnemonic |
|---|---|---|
| electrodeLocationBaseFlag | 1 | bslbf |
| electrodeLocationFlag | 1 | bslbf |
| wavePatternFlag | 1 | bslbf |
| ElectrographSensorBaseAttributesType | | ElectrographSensorBaseAttributesType |
| electrographSensorType | See above | electrographSensorType |
| if (electrodeLocationBaseFlag == 1){ | | |
| electrodeLocationBase | 8 | bslbf |
| } | | |

TABLE 43-continued

| EEGSensorType{ | Number of bits | Mnemonic |
|---|---|---|
|   if (electrodeLocationFlag == 1){ | | |
|     electrodeLocation | 8 | bslbf |
|   } | | |
|   if (wavePatternFlag == 1){ | | |
|     wavePattern | 4 | bslbf |
|   } | | |
| } | | |

Table 44 shows additional semantics for the binary representation of the EEG sensor type, according to example embodiments.

TABLE 44

| Name | Definition |
|---|---|
| electrodeLocationBaseFlag | This field, which is only present in the binary representation, signals whether electrodeLocationBase attributes are specified. A value of "1" means the attributes shall be used, and "0" means the attributes shall not be used. |
| electrodeLocationFlag | This field, which is only present in the binary representation, signals whether electrodeLocationFlag attributes are specified. A value of "1" means the attributes shall be used, and "0" means the attributes shall not be used. |
| wavePatternFlag | This field, which is only present in the binary representation, signals whether wavePatternFlag attributes are specified. A value of "1" means the attributes shall be used, and "0" means the attributes shall not be used. |
| electrodeLocationBase | describes a location of a base electrode as a reference to a classification scheme term which is provided by ElectrodeLocationCS defined in A.2.X of ISO/IEC 23005-6. |
| electrodeLocation | describes a location of a base electrode as a reference to a classification scheme term which is provided by ElectrodeLocationCS defined in A.2.X of ISO/IEC 23005-6. Note that these attributes may use the binary representation table for electrodeLocationBase, identically. |
| wavePattern | describes a pattern of a wave sensed as a reference to a classification scheme term which is provided by WavePatternCS defined in A.2.X of ISO/IEC 23005-6. |

Table 45 shows a binary representation of the electrodeLocationBase field and an electrode location type, according to example embodiments.

TABLE 45

| Binary representation (8 bits) | Electrode location type |
|---|---|
| 0 | reserved |
| 1 | EEG Frontal Pole 1 |
| 2 | EEG Frontal Pole 2 |
| 3 | EEG Frontal 3 |
| 4 | EEG Frontal 4 |
| 5 | EEG Central 3 |
| 6 | EEG Central 4 |
| 7 | EEG Parietal 3 |
| 8 | EEG Parietal 4 |
| 9 | EEG Occipital 1 |
| 10 | EEG Occipital 2 |
| 11 | EEG Anterior temporal 7 |
| 12 | EEG Anterior temporal 8 |
| 13 | EEG Middle temporal 3 |
| 14 | EEG Middle temporal 4 |
| 15 | EEG Posterior temporal 5 |
| 16 | EEG Posterior temporal 6 |
| 17 | EEG Midline-Frontal |
| 18 | EEG Midline-Central |
| 19 | EEG Midline-Parietal |
| 20 | EEG Auricular 1 |
| 21 | EEG Auricular 2 |
| 22 | ECG Right Arm |
| 23 | ECG Left Arm |
| 24 | ECG Right Leg |
| 25 | ECG Left Leg |
| 26 | ECG V1 |
| 27 | ECG V2 |
| 28 | ECG V3 |
| 29 | ECG V4 |
| 30 | ECG V5 |
| 31 | ECG V6 |
| 32 | EOG A |
| 33 | EOG B |
| 34 | EOG C |
| 35 | EOG D |
| 36 | EOG E |
| 37-255 | reserved |

Table 46 shows a binary representation of the wave pattern field and a wave pattern type, according to example embodiments.

TABLE 46

| Binary representation (4 bits) | Wave pattern Type |
|---|---|
| 0 | reserved |
| 1 | EEG Delta |
| 2 | EEG Theta |
| 3 | EEG Alpha |
| 4 | EEG Beta |
| 5 | EEG Gamma |
| 6-16 | reserved |

Table 47 shows Source 11, as an example.

TABLE 47

```
<!--######################################-->
<!--Definition of ECG Sensor type -->
<!--######################################-->
<complexType name="ECGSensorType">
    <complexContent>
        <extension base="iidl:SensedInfoBaseType">
            <attribute name="array_value" type="mpeg7:FloatMatrixType" use=" required "/>
            <attribute name="unit" type="mpegvct:unitType" use="optional"/>
        </extension>
```

TABLE 47-continued

```
    </complexContent>
</complexType>
```

Source 11 shows sensed information with respect to an ECG sensor, using XML, for example. However, a program source of Source 11 is provided only as an example, and example embodiments are not limited thereto.

An ECG sensor type may correspond to a tool to describe sensed information with respect to the ECG sensor.

The ECG sensor type may include at least one of attributes of a timestamp, a unit, and an array value.

The timestamp denotes information about a sensing time of the ECG sensor.

The unit denotes information about a unit of the sensed information of the ECG sensor.

The array value denotes information about a value sensed by the ECG sensor. For example, the array value may be sensed in units of millivolts (mV).

Table 48 shows Example 10.

TABLE 48

```
<iidl:SensedInfo xsi:type="iidl:ECGSensorType" id="ECGS001"
sensorIdRef="ECGSID001" activate="true" timestamp="100.0">
    <iidl:array_value n1:dim="12">10.3 9.8 10.1 5.3 1.0 4.5 10.7 9.8
11.2 7.7 12.2 5.5</iidl:array_value>
</iidl:SensedInfo>
```

Example 10 shows an example of the ECG sensor type. However, Example 10 is provided as only an example of the ECG sensor type, and example embodiments are not limited thereto.

Table 49 shows a binary representation syntax of the ECG sensor type, according to example embodiments.

TABLE 49

| ECGSensorType{ | Number of bits | Mnemonic |
|---|---|---|
| ElectrographSensorBaseAttributesType | | Electrograph-SensorBase-AttributesType |
| electrographSensorType | See above | electrograph-SensorType |
| } | | |

Table 50 shows Source 12, as an example.

TABLE 50

```
<!--###################################-->
<!--Definition of EMG Sensor type -->
<!--###################################-->
<complexType name="EMGSensorType">
    <complexContent>
        <extension base="iidl:SensedInfoBaseType">
            <attribute name="array_value" type="mpeg7:FloatMatrixType" use=" required "/>
            <attribute name="unit" type="mpegvct:unitType" use="optional"/>
        </extension>
    </complexContent>
</complexType>
```

Source 12 shows sensed information with respect to an EMG sensor, using XML, for example. However, a program source of Source 12 is provided only as an example, and example embodiments are not limited thereto.

An EMG sensor type may correspond to a tool to describe sensed information with respect to the EMG sensor.

The EMG sensor type may include at least one of attributes of a timestamp, a unit, and an array value.

The timestamp denotes information about a sensing time of the EMG sensor.

The units denote information about units of the sensed information of the EMG sensor.

The array value denotes information about a value sensed by the EMG sensor. For example, the array value may be sensed in units of mV.

Table 51 shows Example 11.

TABLE 51

```
<iidl:SensedInfo xsi:type="iidl:EMGSensorType" id="EMGS001"
sensorIdRef="EMGSID001" activate="true" timestamp="100.0">
    <iidl:array_value n1:dim="3">15.7 10.4 12.1</iidl:array_value>
</iidl:SensedInfo>
```

Example 11 shows an example of the EMG sensor type. However, Example 11 is provided as only an example of the EMG sensor type, and example embodiments are not limited thereto.

Table 52 shows a binary representation syntax of the EMG sensor type, according to example embodiments.

TABLE 52

| EMGSensorType{ | Number of bits | Mnemonic |
|---|---|---|
| ElectrographSensorBaseAttributesType | | Electrograph-SensorBase-AttributesType |
| electrographSensorType | See above | electrograph-SensorType |
| } | | |

Table 53 shows Source 13, as an example.

TABLE 53

```
<!--###################################-->
<!--Definition of EOG Sensor type -->
<!--###################################-->
<complexType name="EOGSensorType">
    <complexContent>
        <extension base="iidl:SensedInfoBaseType">
            <attribute name="array_value" type="mpeg7:FloatMatrixType" use=" required "/>
            <attribute name="unit" type="mpegvct:unitType" use="optional"/>
        </extension>
    </complexContent>
</complexType>
```

Source 13 shows sensed information with respect to an EOG sensor, using XML, for example. However, a program source of Source 13 is provided only as an example, and example embodiments are not limited thereto.

An EOG sensor type may correspond to a tool to describe sensed information with respect to the EOG sensor.

The EOG sensor type may include at least one of attributes of a timestamp, a unit, and an array value.

The timestamp denotes information about a sensing time of the EOG sensor.

The unit denotes information about a unit of the sensed information of the EOG sensor.

The array value denotes information about a value sensed by the EOG sensor. For example, the array value may be sensed in units of microvolts (μV).

Table 54 shows Example 12.

TABLE 54

<iidl:SensedInfo xsi:type="iidl:EOGSensorType" id="EOGS001" sensorIdRef="EOGSID001" activate="true" timestamp="100.0">
    <iidl:array_value n1:dim="6">[134.5 1001.8 523.8 421.3 157.9 200.5</iidl:array_value>
</iidl:SensedInfo>

Example 12 shows an example of the EOG sensor type. However, Example 12 is provided as only an example of the EOG sensor type, and example embodiments are not limited thereto.

Table 55 shows a binary representation syntax of the EOG sensor type, according to example embodiments.

TABLE 55

| EOGSensorType{ | Number of bits | Mnemonic |
|---|---|---|
| electrodeLocationBaseFlag | 1 | bslbf |
| electrodeLocationFlag | 1 | bslbf |
| ElectrographSensorBaseAttributesType | | ElectrographSensorBaseAttributesType |
| electrographSensorType | See above | electrographSensorType |
| if (electrodeLocationBaseFlag == 1){ | | |
|    electrodeLocationBase | 8 | bslbf |
| } | | |
| if (electrodeLocationFlag == 1){ | | |
|    electrodeLocation | 8 | bslbf |
| } | | |
| } | | |

Table 56 shows additional semantics for the binary representation of the EOG sensor type, according to example embodiments.

TABLE 56

| Name | Definition |
|---|---|
| electrodeLocationBaseFlag | This field, which is only present in the binary representation, signals whether electrodeLocationBase attributes are specified. A value of "1" means the attributes shall be used, and "0" means the attributes shall not be used. |
| electrodeLocationFlag | This field, which is only present in the binary representation, signals whether electrodeLocationFlag attributes are specified. A value of "1" means the attributes shall be used, and "0" means the attributes shall not be used. |
| electrodeLocationBase | describes a location of a base electrode as a reference to a classification scheme term which is provided by ElectrodeLocationCS defined in A.2.X of ISO/IEC 23005-6. |
| electrodeLocation | describes a location of a base electrode as a reference to a classification scheme term which is provided by ElectrodeLocationCS defined in A.2.X of ISO/IEC 23005-6. |

Note that these attributes may use the binary representation table for electrodeLocationBase, identically.

Table 57 shows a binary representation of the electrodeLocationBase field and an electrode location type, according to example embodiments.

TABLE 57

| Binary representation (8 bits) | Electrode location type |
|---|---|
| 0 | reserved |
| 1 | EEG Frontal Pole 1 |
| 2 | EEG Frontal Pole 2 |
| 3 | EEG Frontal 3 |
| 4 | EEG Frontal 4 |
| 5 | EEG Central 3 |
| 6 | EEG Central 4 |
| 7 | EEG Parietal 3 |
| 8 | EEG Parietal 4 |
| 9 | EEG Occipital 1 |
| 10 | EEG Occipital 2 |
| 11 | EEG Anterior temporal 7 |
| 12 | EEG Anterior temporal 8 |
| 13 | EEG Middle temporal 3 |
| 14 | EEG Middle temporal 4 |
| 15 | EEG Posterior temporal 5 |
| 16 | EEG Posterior temporal 6 |
| 17 | EEG Midline-Frontal |
| 18 | EEG Midline-Central |
| 19 | EEG Midline-Parietal |
| 20 | EEG Auricular 1 |
| 21 | EEG Auricular 2 |
| 22 | ECG Right Arm |
| 23 | ECG Left Arm |
| 24 | ECG Right Leg |
| 25 | ECG Left Leg |
| 26 | ECG V1 |
| 27 | ECG V2 |
| 28 | ECG V3 |
| 29 | ECG V4 |
| 30 | ECG V5 |
| 31 | ECG V6 |
| 32 | EOG A |
| 33 | EOG B |
| 34 | EOG C |
| 35 | EOG D |
| 36 | EOG E |
| 37-255 | reserved |

Table 58 shows Source 14, as an example.

TABLE 58

<!--###################################### -->
<!--Definition of GSR Sensor type -->
<!--###################################### -->
<complexType name="GSRSensorType">
   <complexContent>
      <extension base="iidl:SensedInfoBaseType">
         <attribute name="array_value" type=" mpeg7:FloatMatrixType" use=" required "/>
         <attribute name="unit" type="mpegvct:unitType" use="optional"/>
      </extension>
   </complexContent>
</complexType>

Source 14 shows sensed information with respect to a GSR sensor, using XML, for example. However, a program source of Source 14 is provided only as an example, and example embodiments are not limited thereto.

A GSR sensor type may correspond to a tool to describe sensed information with respect to the GSR sensor.

The GSR sensor type may include at least one of attributes of a timestamp, a unit, and an array value.

The timestamp denotes information about a sensing time of the GSR sensor.

The unit denotes information about a unit of the sensed information of the GSR sensor.

The array value denotes information about a value sensed by the GSR sensor. For example, the array value may be sensed in units of micromhos (μʊ).

Table 59 shows Example 13.

TABLE 59

<iidl:SensedInfo xsi:type="iidl:GSRSensorType" id="GSRS001" sensorIdRef="GSRSID001" activate="true" timestamp="100.0">
    <iidl:array_value n1:dim="2">0.3 0.5</iidl:array_value>
</iidl:SensedInfo>

Example 13 shows an example of the GSR sensor type. However, Example 13 is provided as only an example of the GSR sensor type, and example embodiments are not limited thereto.

Table 60 shows a binary representation syntax of the GSR sensor type, according to example embodiments.

TABLE 60

| ElectrographSensorType{ | Number of bits | Mnemonic |
|---|---|---|
| unitFlag | 1 | bslbf |
| SensedInfoBaseType | See above | SensedInfoBaseType |
| dimX | 16 | uimsbf |
| dimY | 16 | uimsbf |
| for(k = 0; k< dimX; k++){ | | |
|   for(j=0;j< dimY;j++){ | | |
|     array_value[(k−1)* dimY + j] | 32 | fsbf |
|   } | | |
| } | | |
| If (unitFlag == 1){ | | |
|   unit | | unitType |
| } | | |
| } | | |

Table 61 shows additional semantics for the binary representation of the GSR sensor type, according to example embodiments.

TABLE 61

| Name | Definition |
|---|---|
| unitFlag | This field, which is only present in the binary representation, signals that a unit other than a default unit is being used. A value of "1" means that the unit being used is specified in unit attributes, and "0" means that the default unit is being used. |
| dimX | This field, which is only present in the binary representation, indicates a number of sensing locations. |

TABLE 61-continued

| Name | Definition |
|---|---|
| dimY | This field, which is only present in the binary representation, indicates a number of pieces of time series-sensed information with respect to each sensing location. |

Table 62 shows Source 15, as an example.

TABLE 62

<!-- ################################################ -->
<!-- Definition of bio sensor Type                -->
<!-- ################################################ -->
<complexType name="BioSensorType">
<complexContent>
<extension base="iidl:SensedInfoBaseType">
<sequence>
<element name="BodyHeight" type="iidl:BodyHeightSensorType" minOccurs="0"/>
<element name="BodyWeight" type="iidl:BodyWeightSensorType" minOccurs="0"/>
<element name="BodyTemperature" type="iidl:BodyTemperatureSensorType" minOccurs="0"/>
<element name="BodyFat" type="iidl:BodyFatSensorType" minOccurs="0"/>
<element name="BloodType" type="iidl:BloodTypeSensorType" minOccurs="0"/>
<element name="BloodPressure" type="iidl:BloodPressureSensorType" minOccurs="0"/>
<element name="BloodSugar" type="iidl:BloodSugarSensorType" minOccurs="0"/>
<element name="BloodOxygen" type="iidl:BloodOxygenSensorType" minOccurs="0"/>
<element name="HeartRate" type="iidl:HeartRateSensorType" minOccurs="0"/>
<element name="EEG" type="iidl:EEGSensorType" minOccurs="0"/>
<element name="ECG" type="iidl:ECGSensorType" minOccurs="0"/>
<element name="EMG" type="iidl:EMGSensorType" minOccurs="0"/>
<element name="EOG" type="iidl:EOGSensorType" minOccurs="0"/>
<element name="GSR" type="iidl:GSRSensorType" minOccurs="0"/>
</sequence>
</extension>
</complexContent>
</complexType>

Source 15 shows sensed information with respect to a bio sensor, using XML, for example. However, a program source of Source 15 is provided only as an example, and example embodiments are not limited thereto.

A bio sensor type may correspond to a tool to describe sensed information with respect to the bio sensor.

The bio sensor type may include at least one of attributes of a body height, a body weight, a body temperature, a body fat, a blood type, a blood pressure, a blood sugar, a blood oxygen, a heart rate, an EEG, an ECG, an EMG, an EOG, and GSR. These bio sensor types are exemplary, and thus, the present disclosure is not limited thereto.

Table 63 shows a binary representation syntax of the bio sensor type, according to example embodiments.

TABLE 63

| BioSensorType { | Number of bits | Mnemonic |
|---|---|---|
| BodyHeightFlag | 1 | bslbf |
| BodyWeightFlag | 1 | bslbf |
| BodyTemperatureFlag | 1 | bslbf |
| BodyFatFlag | 1 | bslbf |
| BloodTypeFlag | 1 | bslbf |
| BloodPressureFlag | 1 | bslbf |
| BloodSugarFlag | 1 | bslbf |
| BloodOxygenFlag | 1 | bslbf |
| HeartRateFlag | 1 | bslbf |
| EEGFlag | 1 | bslbf |

TABLE 63-continued

| BioSensorType { | Number of bits | Mnemonic |
|---|---|---|
| ECGFlag | 1 | bslbf |
| EMGFlag | 1 | bslbf |
| EOGFlag | 1 | bslbf |
| GSRFlag | 1 | bslbf |
| SensedInfoBaseType | | SensedInfoBaseTypeType |
| if(BodyHeightFlag) { | | |
|    BodyHeight | | BodyHeightSensorType |
| } | | |
| if(BodyWeightFlag) { | | |
|    BodyWeight | | BodyWeightSensorType |
| } | | |
| if(BodyTemperatureFlag) { | | |
|    BodyTemperature | | BodyTemperatureSensorType |
| } | | |
| if(BodyFatFlag) { | | |
|    BodyFat | | BodyFatSensorType |
| } | | |
| if(BloodTypeFlag) { | | |
|    BloodType | | BloodTypeSensorType |
| } | | |
| if(BloodPressureFlag) { | | |
|    BloodPressure | | BloodPressureSensorType |
| } | | |
| if(BloodSugarFlag) { | | |
|    BloodSugar | | BloodSugarSensorType |
| } | | |
| if(BloodOxygenFlag) { | | |
|    BloodOxygen | | BloodOxygenSensorType |
| } | | |
| if(HeartRateFlag) { | | |
|    HeartRate | | HeartRateSensorType |
| } | | |
| if(EEGFlag) { | | |
|    EEG | | EEGSensorType |
| } | | |
| if(ECGFlag) { | | |
|    ECG | | ECGSensorType |
| } | | |
| if(EMGFlag) { | | |
|    EMG | | EMGSensorType |
| } | | |
| if(EOGFlag) { | | |
|    EOG | | EOGSensorType |
| } | | |
| if(GSRFlag) { | | |
|    GSR | | GSRSensorType |
| } | | |
| } | | |

Table 64 shows additional semantics for the binary representation of the bio sensor type, according to example embodiments.

TABLE 64

| Name | Definition |
|---|---|
| BodyHeightFlag | This field, which is only present in the binary representation, signals whether height-sensed information is available. A value of "1" means the sensed information is included, and "0" means the sensed information is not included. |
| BodyWeightFlag | This field, which is only present in the binary representation, signals whether weight-sensed information is available. A value of "1" means the sensed information is included, and "0" means the sensed information is not included. |
| BodyTemperatureFlag | This field, which is only present in the binary representation, signals whether temperature-sensed information is available. A value of "1" means the sensed information is included, and "0" means the sensed information is not included. |
| BodyFatFlag | This field, which is only present in the binary representation, signals whether body fat-sensed information is available. A value of "1" means the sensed information is included, and "0" means the sensed information is not included. |
| BloodTypeFlag | This field, which is only present in the binary representation, signals whether blood type-sensed information is available. A value of "1" means the sensed information is included, and "0" means the sensed information is not included. |
| BloodPressureFlag | This field, which is only present in the binary representation, signals whether blood pressure-sensed information is available. A value of "1" means the sensed information is included, and "0" means the sensed information is not included. |
| BloodSugarFlag | This field, which is only present in the binary representation, signals whether blood sugar-sensed information is available. A value of "1" means the sensed information is included, and "0" means the sensed information is not included. |
| BloodOxygenFlag | This field, which is only present in the binary representation, signals whether blood oxygen-sensed information is available. A value of "1" |

TABLE 64-continued

| Name | Definition |
|---|---|
| | means the sensed information is included, and "0" means the sensed information is not included. |
| HeartRateFlag | This field, which is only present in the binary representation, signals whether heart rate-sensed information is available. A value of "1" means the sensed information is included, and "0" means the sensed information is not included. |
| EEGFlag | This field, which is only present in the binary representation, signals whether EEG-sensed information is available. A value of "1" means the sensed information is included, and "0" means the sensed information is not included. |
| ECGFlag | This field, which is only present in the binary representation, signals whether ECG-sensed information is available. A value of "1" means the sensed information is included, and "0" means the sensed information is not included. |
| EMGFlag | This field, which is only present in the binary representation, signals whether EMG-sensed information is available. A value of "1" means the sensed information is included, and "0" means the sensed information is not included. |
| EOGFlag | This field, which is only present in the binary representation, signals whether EOG-sensed information is available. A value of "1" means the sensed information is included, and "0" means the sensed information is not included. |
| GSRFlag | This field, which is only present in the binary representation, signals whether GSR-sensed information is available. A value of "1" means the sensed information is included, and "0" means the sensed information is not included. |

Table 65 shows Source 16, as an example.

TABLE 65

```
<!--###################################### -->
<!--Definition of Electrograph Sensor type -->
<!--###################################### -->
<complexType name="ElectrographSensorType">
<complexContent>
    <extension base="dfid:SensedInfoBaseType">
      <sequence>
        <element name="WaveValue" type=" mpeg7:FloatMatrixType" minOccurs="1"/>
      </sequence>
      <attribute name="waveformLabel" type="mpeg7:termReferenceType" use="optional"/>
      <attribute name="electrodeLocationBase" type="mpeg7:termReferenceType" use="optional"/>
      <attribute name="electrodeLocation" type="mpeg7:termReferenceType" use="optional"/>
      <attribute name="unit" type="dfid:unitType" use="optional"/>
      <attribute name="maxAmplitude" type=" float" use="optional"/>
      <attribute name="wavePattern" type="mpeg7:termReferenceType" use="optional"/>
    </extension>
</complexContent>
</complexType>
```

Source 16 shows sensed information with respect to an electrograph sensor, using XML, for example. However, a program source of Source 16 is provided only as an example, and example embodiments are not limited thereto.

An electrograph sensor type may correspond to a tool to describe sensed information with respect to the electrograph sensor.

The electrograph sensor type may include at least one of attributes of a timestamp, a waveform label, an electrode location base, an electrode location, a wave value, a unit, a maximum amplitude, and a wave pattern.

The timestamp denotes information about a sensing time of the electrograph sensor.

The waveform label describes a label of a based waveform. The waveform label may reference a classification scheme term which is provided by an electrography classification scheme. The electrography classification scheme may be defined in A.2.X of ISO/IEC 23005-6.

The electrode location base describes a location of a base electrode. The electrode location base may reference a classification scheme term which is provided by the electrography classification scheme. The electrography classification scheme may be defined in A.2.X of ISO/IEC 23005-6.

The electrode location may describe a location of a base electrode. The electrode location base may reference a classification scheme term which is provided by the electrography classification scheme. The electrography classification scheme may be defined in A.2.X of ISO/IEC 23005-6.

The wave value denotes a time series-sensed value of the electrograph sensor, in units of microvolts (μV).

The unit describes a unit of a sensed value with respect to both the wave value and a maximum amplitude when another unit, other than a default unit, is used. The unit may reference a classification scheme term which is provided by the electrography classification scheme. The electrography classification scheme may be defined in A.2.X of ISO/IEC 23005-6.

The maximum amplitude denotes a maximum amplitude of the electrograph sensor, in units of μV.

The wave pattern may describe a pattern of a sensed wave. The wave pattern may reference a classification scheme term which is provided by the electrography classification scheme. The electrography classification scheme may be defined in A.2.X of ISO/IEC 23005-6.

A location for measuring an electrical activity between two electrodes will be described in detail with reference to FIGS. 12 and 13.

The electrical activity may create a waveform between the two electrodes. For example, a first waveform may be obtained from two electrodes FP1 and F7, as shown in FIG. 12.

In order to identify each waveform, it may be necessary to know which of the two locations are used.

Table 66 shows types of waveforms classified based on a frequency, according to example embodiments.

TABLE 66

Alpha waveform: waveform having frequency ranging from 8 to13 Hz
Beta waveform: waveform having frequency ranging from 13 to 30 Hz
Theta waveform: waveform having frequency ranging from 4 to8 Hz
Delta waveform: waveform having frequency ranging from 0.5 to 4 Hz Table 67 shows a classification scheme for waveform patterns, according to example embodiments.

TABLE 67

```
<ClassificationScheme
uri="urn:mpeg:mpeg-v:01-CI-WavePatternCS-NS">
    <Term termID="EEG_Delta">
        <Name xml:lang="en">EEG Delta</Name>
        <Definition xml:lang="en">Describes the wave pattern
which is the frequency range up to 4 Hz and tends to be the highest
in amplitude and the slowest waves</Definition>
    </Term>
    <Term termID="EEG_Theta">
        <Name xml:lang="en">EEG Theta</Name>
        <Definition xml:lang="en">Describes the wave pattern
which is the frequency range from 4 Hz to 7 Hz</Definition>
```

TABLE 67-continued

```
    </Term>
<Term termID="EEG_Alpha">
        <Name xml:lang="en">EEG Alpha</Name>
        <Definition xml:lang="en"> Describes the wave pattern
which is the frequency range from 8 Hz to 12 Hz</Definition>
</Term>
<Term termID="EEG_Beta">
        <Name xml:lang="en">EEG Beta</Name>
        <Definition xml:lang="en"> Describes the wave
pattern which is the frequency range from 12 Hz to about 30 Hz and
is seen usually on both sides in symmetrical distribution and is
most evident frontally</Definition>
</Term>
        <Term termID="EEG_Gamma">
            <Name xml:lang="en">EEG Gamma</Name>
            <Definition xml:lang="en"> Describes the wave pattern
        which is the frequency range approximately 30-100 Hz. </Definition>
        </Term>
    </ClassificationScheme>
```

A maximum amplitude of a waveform may be used to indicate an intensity of the activity.

The sensed information with respect to the electrograph sensor may include time series electrical potential data, labels corresponding to two electrode locations, waveform classification based on patterns of the waveform, and a maximum amplitude.

Table 68 shows a binary representation syntax of the electrograph sensor type, according to example embodiments.

TABLE 68

| ElectrographSensorType{ | Number of bits | Mnemonic |
|---|---|---|
| unitFlag | 1 | bslbf |
| SensedInfoBaseType | See above | SensedInfoBaseType |
| dimX | 16 | uimsbf |
| dimY | 16 | uimsbf |
| for(k = 0; k< dimX; k++){ | | |
|     for(j=0;j< dimY;j++){ | | |
|         WaveValue[(k−1)* dimY + j] | 32 | fsbf |
|     } | | |
| } | | |
| If (unitFlag == 1){ | | |
|     unit | | unitType |
| } | | |
| } | | |

| ElectrographSensorBaseAttributesType{ | Number of bits | Mnemonic |
|---|---|---|
| waveformLabel | 8 | bslbf |
| maxAmplitude | 32 | fsbf |
| } | | |

Table 69 shows additional semantics for the binary representation of the electrograph sensor type, according to example embodiments.

TABLE 69

| Name | Definition |
|---|---|
| unitFlag | This field, which is only present in the binary representation, signals that a unit other than a default unit is being used. A value of "1" means that the unit being used is specified in unit attributes, and "0" means that the default unit is being used. |
| dimX | This field, which is only present in the binary representation, indicates a number of sensing locations. |

TABLE 69-continued

| Name | Definition |
|---|---|
| dimY | This field, which is only present in the binary representation, indicates a number of pieces of sensed information with respect to each sensing location. |
| waveformLabel | describes a label of a waveform by referencing a classification scheme term which is provided by ElectrographyLabelCS defined in A.2.X of ISO/IEC 23005-6. |

Table 70 shows a binary representation of the waveformLabel field and a waveform type, according to example embodiments.

TABLE 70

| Binary representation (8 bits) | Waveform Type |
|---|---|
| 0 | reserved |
| 1 | EEG between FP1 and F7 |
| 2 | EEG between F7 and T3 |
| 3 | EEG between T3 and T5 |
| 4 | EEG between T5 and O1 |
| 5 | EEG between FP2 and F8 |
| 6 | EEG between F8 and T4 |
| 7 | EEG between T4 and T6 |
| 8 | EEG between T6 and O2 |
| 9 | EEG between FP1 and F3 |
| 10 | EEG between F3 and C3 |
| 11 | EEG between C3 and P3 |

TABLE 70-continued

| Binary representation (8 bits) | Waveform Type |
|---|---|
| 12 | EEG between P3 and O1 |
| 13 | EEG between FP2 and F4 |
| 14 | EEG between F4 and C4 |
| 15 | EEG between C4 and P4 |
| 16 | EEG between P4 and O2 |
| 17 | EEG between FZ and CZ |
| 18 | EEG between CZ and PZ |
| 19 | ECG I |
| 20 | ECG II |
| 21 | ECG III |
| 22 | ECG augmented vector right |
| 23 | ECG augmented vector left |

TABLE 70-continued

| Binary representation (8 bits) | Waveform Type |
| --- | --- |
| 24 | ECG augmented vector foot |
| 25 | ECG V1 |
| 26 | ECG V2 |
| 27 | ECG V3 |
| 28 | ECG V4 |
| 29 | ECG V5 |
| 30 | ECG V6 |
| 31 | EMG Smaller Face Muscles |
| 32 | EMG Smaller Neck Muscles |
| 33 | EMG Pectoralis Minor |
| 34 | EMG Diaphragma |
| 35 | EMG Smaller Forearm Muscles |
| 36 | EMG Transversus Abdominis |
| 37 | EMG Iliacus |
| 38 | EMG Psoas major |
| 39 | EMG Adductors |
| 40 | EMG Vastus Intermedius |
| 41 | EMG Thin Deep Shank Muscles |
| 42 | EMG Smaller Foot Muscles |
| 43 | EMG Deep Neck Muscles |
| 44 | EMG Supraspinatus |
| 45 | EMG Subscapularis |
| 46 | EMG Rhomboideus |
| 47 | EMG Teres Major Minor |
| 48 | EMG Thoracic Erector Spinae |
| 49 | EMG Triceps Brachii C Med |
| 50 | EMG Deep Segmental Erector Spinae |
| 51 | EMG Quadratus Lumborum |
| 52 | EMG Smaller Forearm Extensors |
| 53 | EMG Deep Multifii |
| 54 | EMG Deep Hip Muscles |
| 55 | EMG Thin/Deep Shank Muscles |
| 56 | EMG Frontalis |
| 57 | EMG Masseter |
| 58 | EMG Sternocleidomastoideus |
| 59 | EMG Deltoideus p. Acromialis |
| 60 | EMG Deltoideus p. Clavicularis |
| 61 | EMG Pectoralis Major |
| 62 | EMG Biceps Brachii |
| 63 | EMG Serratus Anterior |
| 64 | EMG Rectus Abdominis |
| 65 | EMG Brachioradialis |
| 66 | EMG Flexor Carpum Radialis |
| 67 | EMG Flexor Carpum Ulnaris |
| 68 | EMG Obliquus Externus Abdominis |
| 69 | EMG Internus Transversus Abdominis |
| 70 | EMG Tensor Fascia Latae |
| 71 | EMG Interosseus |
| 72 | EMG Adductores |
| 73 | EMG Rectus Femoris |
| 74 | EMG Vastus Lateralis |
| 75 | EMG Vastus Medialis |
| 76 | EMG Peroneus Longus |
| 77 | EMG Tibialis Anterior |
| 78 | EMG Neck Extensors |
| 79 | EMG Trapezius P. Descendenz |
| 80 | EMG Trapezius P. Transversus |
| 81 | EMG Deltoideus P. Scapularis |
| 82 | EMG Infraspinatus |
| 83 | EMG Trapezius P. Ascendenz |
| 84 | EMG Triceps Brachii |
| 85 | EMG Latissimus Dorsi |
| 86 | EMG Erector Spinae Thoracic Region |
| 87 | EMG Erector Spinae Lumbar Region |
| 88 | EMG Smaller Forcearm Extensors |
| 89 | EMG Multifidus Lumbar Region |
| 90 | EMG Glutaeus Medius |
| 91 | EMG Glutaeus Maximus |
| 92 | EMG Biceps Femoris |
| 93 | EMG Semitendinosus |
| 94 | EMG Gastrocnemius Lat. |
| 95 | EMG Gastrocemius Med. |
| 96 | EMG Soleus |
| 97-255 | reserved |

Figure 11:
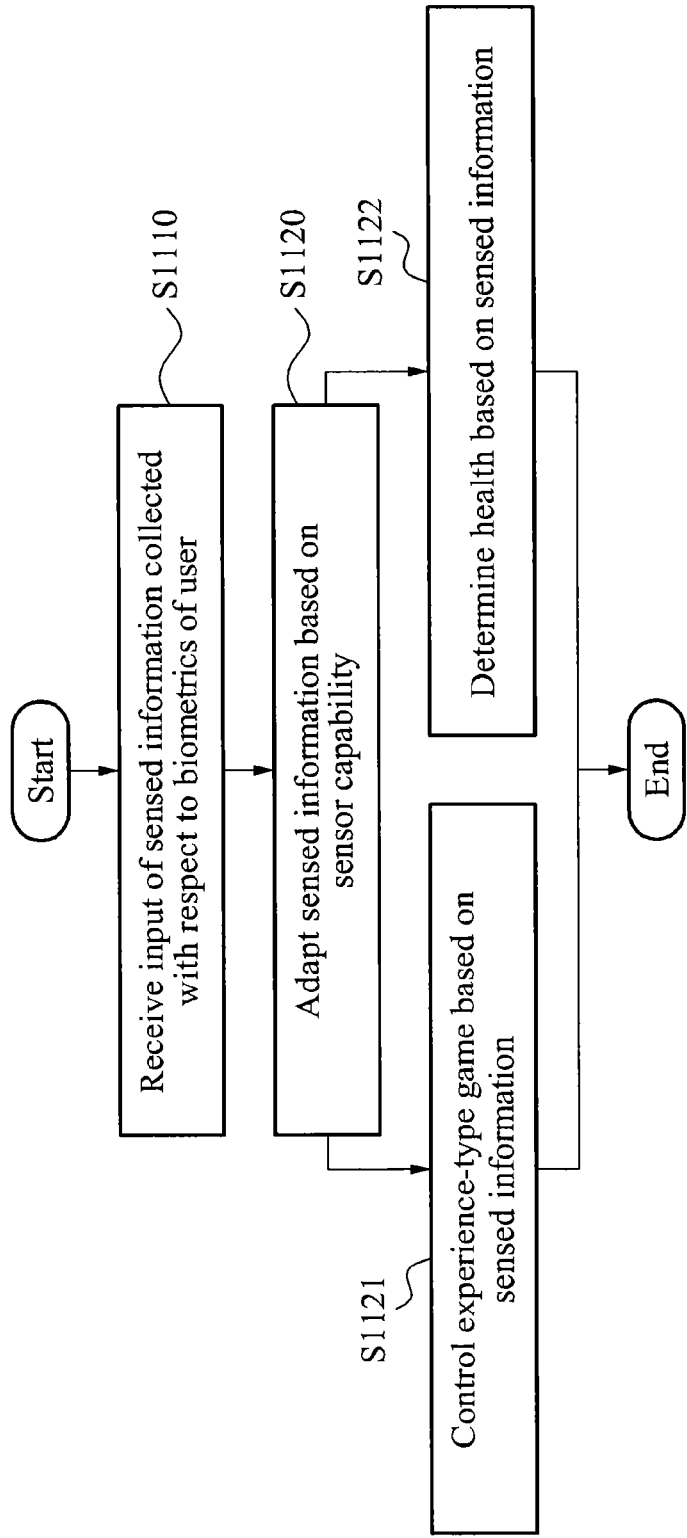
FIG. 11 illustrates an operating method of a virtual world processing apparatus, according to example embodiments.

FIG. 11 illustrates an operating method of a virtual world processing apparatus, according to example embodiments.

Referring to FIG. 11, the virtual world processing apparatus may enable interoperability between a virtual world and a real world, or interoperability between virtual worlds. In S1110, the virtual world processing apparatus may receive an input of sensed information collected by a bio sensor with respect to biometrics of a user in the real world.

For example, the virtual world processing apparatus may receive an input of VR object data indicating information about a virtual object in the real world. In addition, the virtual world processing apparatus may further receive an input of a sensor adaptation preference for controlling the sensed information.

In operation S1120, the virtual world processing apparatus may adapt the sensed information based on a sensor capability associated with a capability of the bio sensor.

For example, when sensed information of 80 kg is collected as a result of sensing a body weight of the user in the real world using a body weight sensor, the virtual world processing apparatus may receive an input of the sensed information of 80 kg. In this instance, when a maxValue of sensor capability with respect to the body weight sensor, corresponds to 70 kg, the virtual world processing apparatus may adapt the sensed information of 80 kg to the maxValue of 70 kg. In addition, the virtual world processing apparatus may apply the sensed information of 70 kg adapted, to the virtual world.

According to example embodiments, the virtual world processing apparatus may adapt the VR object data by applying the sensed information adapted, to the VR object data, thereby generating another piece of VR object data.

According to example embodiments, the virtual world processing apparatus may adapt the sensed information, based on the sensor capability and the sensor adaptation preference.

In operation S1121, the virtual world processing apparatus may control an experience-type game played in the virtual world, based on the sensed information adapted.

For example, the virtual world processing apparatus may generate the other piece of the VR object data by applying the sensed information adapted, to the VR object data indicating information about the virtual object in the experience-type game, and may apply the other piece of the VR object data generated to the experience-type game, thereby controlling the experience-type game.

In operation S1122, the virtual world processing apparatus may determine a health of the user in the real world, based on the sensed information adapted. In addition, the virtual world processing apparatus may provide the user with the determined health of the user.

Figure 12:
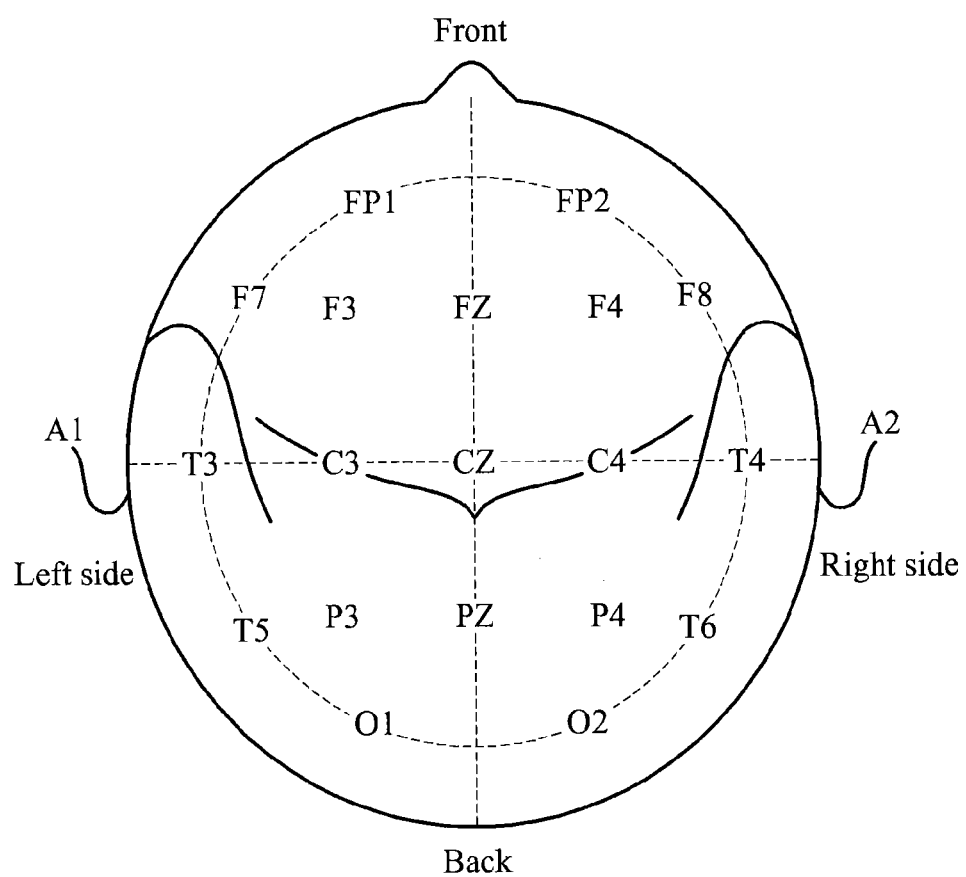
FIG. 12 illustrates location names used in a 10-20 system for electroencephalography (EEG), according to example embodiments.

FIG. 12 illustrates location names used in a 10-20 system for EEG, according to example embodiments.

Referring to FIG. 12, symbols of FP1 and FP2 denote a frontal pole. Symbols of F3 and F4 denote a frontal lobe. Symbols of C3 and C4 denotes a central lobe. Symbols of P3 and P4 denote a pariental lobe. Symbols of O1 and O2 denote an occipital lobe. Symbols of F7 and F8 denote an anterior temporal lobe. Symbols of T3 and T4 denote a middle temporal lobe. Symbols of T5 and T6 denote a posterior temporal lobe. A symbol of FZ denotes a midline-frontal lobe. A symbol of CZ denotes a midline-central lobe. A symbol of PZ denotes a midline-pariental lobe. Symbols of A1 and A2 denotes an auricular lobe.

That is, first letters of F, T, C, P, and O denote frontal, temporal, central, pariental, and occipital lobes, respectively. A latter letter of Z denotes an electrode positioned in the center. Even numbers, for example, 2, 4, 6, and 8, among latter letters, denote electrodes positioned in a right hemisphere. Odd numbers, for example, 1, 3, 5, and 7, among the latter letters, denote electrodes positioned in a left hemisphere.

Figure 13:
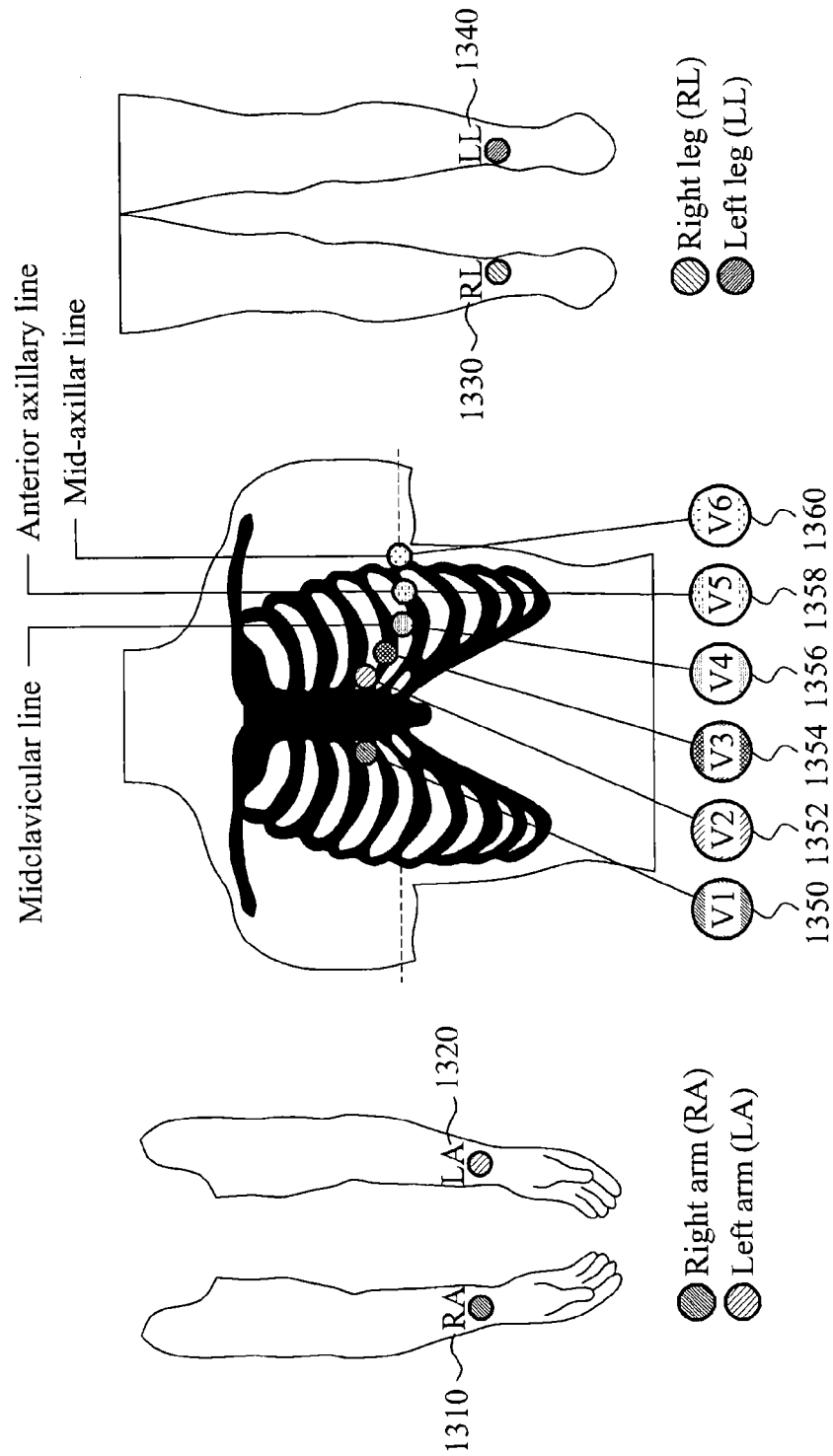
FIG. 13 illustrates location names used in a 12-lead electrocardiography (ECG) system, according to example embodiments.

FIG. 13 illustrates location names used in a 12-lead ECG system, according to example embodiments.

An ECG may include a location map that is widely used to indicate electrodes. Acronyms of each location are illustrated in FIG. 13.

Based on the foregoing information, each label in the 12-lead system may have predetermined locations of the electrodes.

For example, $V_1$ may be obtained from a unipolar electrode at a location of $V_1$.

Table 71 describes electrode labels and electrode placement, according to example embodiments.

TABLE 71

| Electrode label | Electrode placement |
| --- | --- |
| RA 1310 | On the right arm, avoiding bony prominences. |
| LA 1320 | In the same location that RA 1310 was placed, but on the left arm this time |
| RL 1330 | On the right leg, avoiding bony prominences. |
| LL 1340 | In the same location that RL 1330 was placed, but on the left leg this time |
| $V_1$ 1350 | In the fourth intercostal space (between ribs 4 & 5) just to the right of the sternum (breastbone). |
| $V_2$ 1352 | In the fourth intercostal space (between ribs 4 & 5) just to the left of the sternum |
| $V_3$ 1354 | Between leads $V_2$ 1352 and $V_4$ 1356. |
| $V_4$ 1356 | In the fifth intercostal space (between ribs 5 & 6) in the mid-clavicular line (the imaginary line that extends down from the midpoint of the clavicle (collarbone). |
| $V_5$ 1358 | Horizontally even with $V_4$ 1356, but in the anterior axillary line. (The anterior axillary line is the imaginary line that runs down from the point midway between the middle of the clavicle and the lateral end of the clavicle; the lateral end of the collarbone is the end closer to the arm.) |
| $V_6$ 1360 | Horizontally even with $V_4$ 1356 and $V_5$ 1358 in the mid-axillary line. (The mid-axillary line is the imaginary line that extends down from the middle of the patient's armpit.) |

Table 72 shows a classification scheme for electrode placement, according to example embodiments.

TABLE 72

```
<ClassificationScheme uri="urn:mpeg:mpeg-v:01-CI-
ElectrodePlacementCS-NS">
    <Term termID="EEG_FP1">
        <Name xml:lang="en">EEG Frontal Pole 1</Name>
        <Definition xml:lang="en">Describes the location on the
left side frontal pole </Definition>
    </Term>
    <Term termID="EEG_FP2">
        <Name xml:lang="en">EEG Frontal Pole 2</Name>
        <Definition xml:lang="en">Describes the location on the
right side frontal pole </Definition>
    </Term>
    <Term termID="EEG_F3">
        <Name xml:lang="en">EEG Frontal 3</Name>
        <Definition xml:lang="en">Describes the location on the
left side frontal </Definition>
    </Term>
    <Term termID="EEG_F4">
        <Name xml:lang="en">EEG Frontal 4</Name>
        <Definition xml:lang="en">Describes the location on the
right side frontal </Definition>
```

TABLE 72-continued

```
    </Term>
    <Term termID="EEG_C3">
        <Name xml:lang="en">EEG Central 3</Name>
        <Definition xml:lang="en">Describes the location on the
left side central </Definition>
    </Term>
    <Term termID="EEG_C4">
        <Name xml:lang="en">EEG Central 4</Name>
        <Definition xml:lang="en">Describes the location on the
right side central </Definition>
    </Term>
    <Term termID="EEG_P3">
        <Name xml:lang="en">EEG Parietal 3</Name>
        <Definition xml:lang="en">Describes the location on the
left side Pariental </Definition>
    </Term>
    <Term termID="EEG_P4">
        <Name xml:lang="en">EEG Parietal 4</Name>
        <Definition xml:lang="en">Describes the location on the
right side parietal </Definition>
    </Term>
    <Term termID="EEG_O1">
        <Name xml:lang="en">EEG Occipital 1</Name>
        <Definition xml:lang="en">Describes the location on the
left side occipital </Definition>
    </Term>
    <Term termID="EEG_O2">
        <Name xml:lang="en">EEG Occipital 2</Name>
        <Definition xml:lang="en">Describes the location on the
right side occipital </Definition>
    </Term>
    <Term termID="EEG_F7">
        <Name xml:lang="en">EEG Anterior temporal 7</Name>
        <Definition xml:lang="en">Describes the location on the
left side anterior temporal </Definition>
    </Term>
    <Term termID="EEG_F8">
        <Name xml:lang="en">EEG Anterior temporal 8</Name>
        <Definition xml:lang="en">Describes the location on the
right side anterior temporal </Definition>
    </Term>
    <Term termID="EEG_T3">
        <Name xml:lang="en">EEG Middle temporal 3</Name>
        <Definition xml:lang="en">Describes the location on the
left side middle temporal </Definition>
    </Term>
    <Term termID="EEG_T4">
        <Name xml:lang="en">EEG Middle temporal 4</Name>
        <Definition xml:lang="en">Describes the location on the
right side middle temporal </Definition>
    </Term>
    <Term termID="EEG_T5">
        <Name xml:lang="en">EEG Posterior temporal 5</Name>
        <Definition xml:lang="en">Describes the location on the
left side posterior temporal </Definition>
    </Term>
    <Term termID="EEG_T6">
        <Name xml:lang="en">EEG Posterior temporal 6</Name>
        <Definition xml:lang="en">Describes the location on the
right side posterior temporal </Definition>
    </Term>
    <Term termID="EEG_FZ">
        <Name xml:lang="en">EEG Midline-Frontal</Name>
        <Definition xml:lang="en">Describes the location on the
midline- frontal </Definition>
    </Term>
    <Term termID="EEG_CZ">
        <Name xml:lang="en">EEG Midline-Central</Name>
        <Definition xml:lang="en">Describes the location on the
midline- central </Definition>
    </Term>
    <Term termID="EEG_PZ">
        <Name xml:lang="en">EEG Midline-Parietal</Name>
        <Definition xml:lang="en">Describes the location on the
midline- parietal </Definition>
    </Term>
    <Term termID="EEG_A1">
        <Name xml:lang="en">EEG Auricular 1</Name>
        <Definition xml:lang="en">Describes the location on the
left side auricular </Definition>
```

TABLE 72-continued

```
</Term>
<Term termID="EEG_A2">
        <Name xml:lang="en">EEG Auricular 2</Name>
        <Definition xml:lang="en">Describes the location on the
right side auricular </Definition>
    </Term>
    <Term termID="ECG_RA">
        <Name xml:lang="en">ECG Right Arm</Name>
        <Definition xml:lang="en">Describes the location on the
right arm, avoiding bony prominences </Definition>
    </Term>
    <Term termID="ECG_LA">
        <Name xml:lang="en">ECG Left Arm</Name>
        <Definition xml:lang="en">Describes the location on the
    left arm, avoiding bony prominences </Definition>
</Term>
<Term termID="ECG_RL">
        <Name xml:lang="en">ECG Right Leg</Name>
        <Definition xml:lang="en">Describes the location on the
right leg, avoiding bony prominences </Definition>
</Term>
<Term termID="ECG_LL">
        <Name xml:lang="en">ECG Left Leg</Name>
        <Definition xml:lang="en">Describes the location on the
left leg, avoiding bony prominences </Definition>
</Term>
<Term termID="ECG_V1">
        <Name xml:lang="en">ECG V1</Name>
        <Definition xml:lang="en">Describes the location in the
    fourth intercostals space (between ribs 4 & 5) just to the right
    of the sternum (breastbone) </Definition>
    </Term>
    <Term termID="ECG_V2">
        <Name xml:lang="en">ECG V2</Name>
        <Definition xml:lang="en">Describes the location in the
    fourth intercostals space (between ribs 4 & 5) just to the left
    of the sternum </Definition>
    </Term>
<Term termID="ECG_V3">
        <Name xml:lang="en">ECG V3</Name>
        <Definition xml:lang="en">Describes the location between
leads ECG_V2 and ECG_V4 </Definition>
</Term>
<Term termID="ECG_V4">
        <Name xml:lang="en">ECG V4</Name>
        <Definition xml:lang="en">Describes the location in the
fifth intercostals space (between ribs 5 & 6) in the mid-clavicular
line (the imaginary line that extends down from the midpoint of
the clavicle (collarbone)) </Definition>
    </Term>
    <Term termID="ECG_V5">
        <Name xml:lang="en">ECG V5</Name>
        <Definition xml:lang="en">Describes the location in the
    fifth intercostals space in the left anterior axillary line (The anterior
    axillary line is the imaginary line that runs down from the point
    midway between the middle of the clavicle and the lateral end of the
    clavicle; the lateral end of the collarbone is the end closer to the
    arm) </Definition>
    </Term>
    <Term termID="ECG_V6">
        <Name xml:lang="en">ECG V6</Name>
        <Definition xml:lang="en">Describes the location in the
    fifth intercostals space in the left mid axillary line (The midaxillary
line is the imaginary line that extends down from the middle of the
patient's armpit)</Definition>
</Term>
</ClassificationScheme>
```

Figure 14:
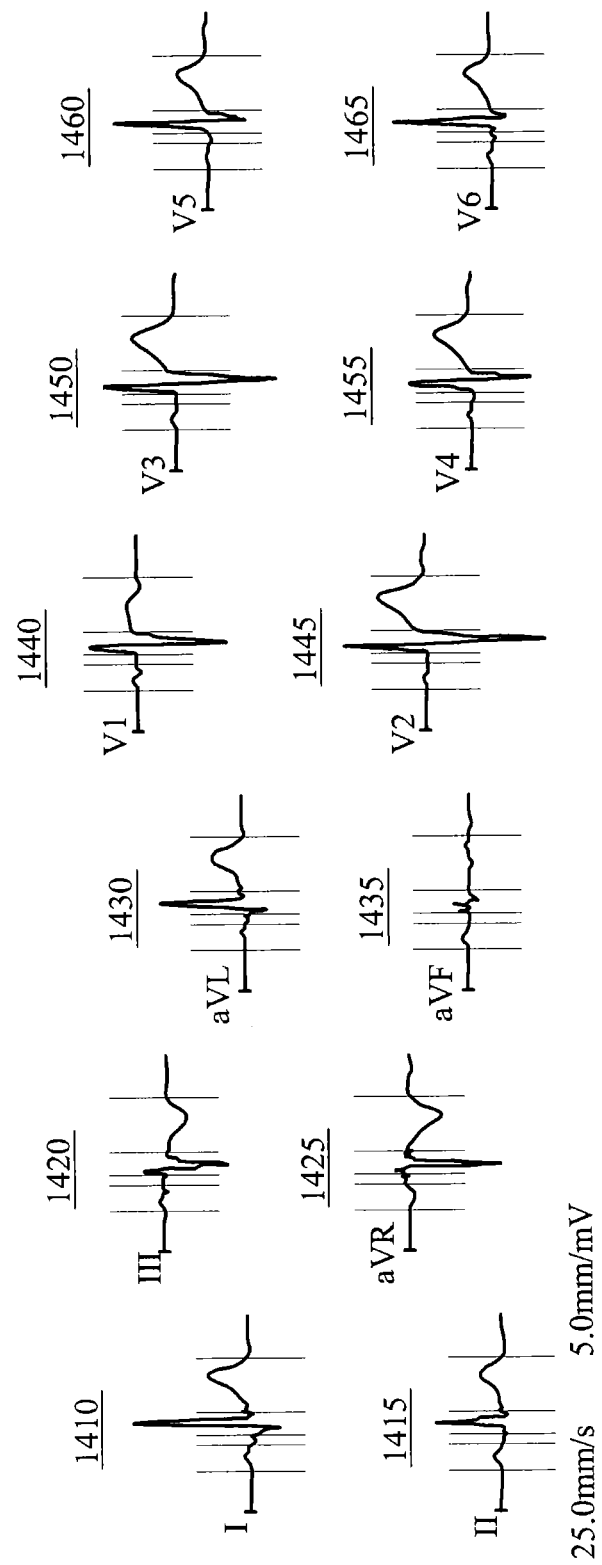
FIG. 14 illustrates 12 leads derived from 10-electrode placement.

FIG. 14 illustrates 12 leads derived from 10-electrode placement, according to example embodiments.

A lead I 1410, a lead II 1415, and a lead III 1420 are limb leads. Electrodes of each of these signals may be placed on limbs, for example, each arm, and a left leg.

The lead I 1410 denotes a voltage between a left arm (LA) electrode and a right arm (RA) electrode.

The lead I 1410 may be computed by Equation 1.

$$I = LA - RA. \quad \text{[Equation 1]}$$

The lead II 1415 denotes a voltage between a left leg (LL) electrode and the RA electrode.

The lead II 1415 may be computed by Equation 2.

$$II = LL - RA. \quad \text{[Equation 2]}$$

The lead III 1420 denotes a voltage between the LL electrode and the LA electrode.

The lead III 1420 may be computed by Equation 3.

$$III = LL - LA. \quad \text{[Equation 3]}$$

Two types of leads may correspond to unipolar and bipolar leads. Bipolar leads may have a single positive pole and a single negative pole. In a 12-lead ECG, the limb leads, for example, the lead I 1410, the lead II 1415, and the lead III 1420, may correspond to bipolar leads. Unipolar leads also may have two poles, however, a negative pole may correspond to a composite pole made up of signals from several other electrodes.

In the 12-lead ECG, leads excluding the limb leads may correspond to unipolar leads. Here, the leads excluding the limb leads may correspond to a lead augmented vector right (aVR) 1425, a lead augmented vector left (aVL) 1430, a lead augmented vector foot (aVF) 1435, a lead $V_1$ 1440, a lead $V_2$ 1445, a lead $V_3$ 1450, a lead $V_4$ 1455, a lead $V_5$ 1460, and a lead $V_6$ 1465.

The lead aVR 1425, the lead aVL 1430, and the lead aVF 1435 may correspond to augmented limb leads. The augmented limb leads may be derived from three electrodes, like the limb leads. However, the augmented limb leads may view a heart from different angles or vectors.

The lead aVR 1425 may have an positive electrode on a right arm. A negative electrode may correspond to a combination of the LA electrode and the LL electrode, which may augment a signal strength of the positive electrode on the right arm.

The lead aVR 1425 may be computed by Equation 4.

$$aVR = RA - \tfrac{1}{2}(LA + LL). \quad \text{[Equation 4]}$$

The lead aVL 1430 may have a positive electrode on a left arm. A negative electrode may correspond to a combination of the RA electrode and the LL electrode, which may augment a signal strength of the positive electrode on the left arm.

The lead aVL 1430 may be computed by Equation 5.

$$aVR = RA - \tfrac{1}{2}(LA + LL). \quad \text{[Equation 5]}$$

The lead aVF 1435 may have a positive electrode on the left leg. A negative electrode may correspond to a combination of the RA electrode and the LL electrode, which may augment a signal strength of the positive electrode on the left leg.

The lead aVF 1435 may be computed by Equation 6.

$$aVF = LL - \tfrac{1}{2}(RA + LA). \quad \text{[Equation 6]}$$

The lead aVR 1425, the lead aVL 1430, and the lead aVF 1435 may be computed based on the limb leads, as expressed by Equation 7.

$$aVR = -\frac{I + II}{2} \quad \text{[Equation 7]}$$

$$aVL = I - \frac{II}{2}$$

$$aVF = II - \frac{I}{2}$$

Electrodes for precordial leads may be placed directly on a chest. Here, the precordial leads may correspond to the lead $V_1$ 1440, the lead $V_2$ 1445, the lead $V_3$ 1450, the lead $V_4$ 1455, the lead $V_5$ 1460, and the lead $V_6$ 1465. Because of close proximity to the heart, the precordial leads may not require augmentation. The precordial leads may view an electrical activity of the heart in a so-called horizontal plane. An electrical axis of the heart in the horizontal plane may be referred to as a Z axis.

Figure 15:
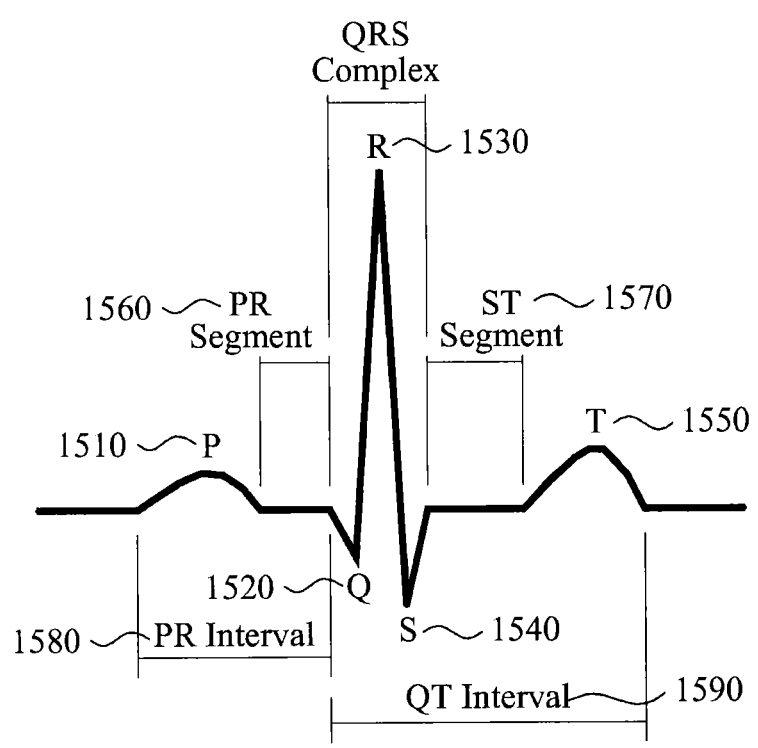
FIG. 15 illustrates a typical waveform of ECG.

FIG. 15 illustrates a typical waveform of ECG, according to example embodiments.

A typical ECG tracing of a cardiac cycle may consist of a P wave 1510, a QRS complex 1595, a T wave 1550, and a U wave, which is normally visible in 50 to 75% of ECGs.

Unlike an EEG, an ECG waveform may correspond to a composite waveform of five different waveforms, for example, the P wave 1510, a Q wave 1520 an R wave 1530, an S wave 1540, and the T wave 1550, in series.

During a normal atrial depolarization, a main electrical vector may be directed from an SA node to an AV node, and may spread from a right atrium to a left atrium. The main electrical vector may be converted into the P wave 1510 on the ECG. Duration of the P wave 1510 may correspond to 80 milliseconds (ms).

The T wave 1550 may represent repolarization or recovery of ventricles. An interval from the beginning of the QRS complex 1595 to an apex of the T wave 1550 may be referred to as an absolute refractory period. A last half of the T wave 1550 may be referred to as a relative refractory period. Duration of the T wave 1550 may correspond to 160 ms.

A PR segment 1560 may connect the P wave 1510 and the QRS complex 1595.

An ST segment 1570 may connect the QRS complex 1595 and the T wave 1550.

A PR interval 1580 may be measured from the beginning of the P wave 1510 to the beginning of the QRS complex 1595.

A QT interval 1590 may be measured from the beginning of the QRS complex 1595 to the end of the T wave 1550.

The QRS complex 1595 may reflect a rapid depolarization of the right and left ventricles. The right and left ventricles may have a large muscle mass when compared to the atria. Accordingly, the QRS complex 1595 may have a much larger amplitude than the P wave 1510.

It may be noted that the time series data of the ECG waveform may not be classified in a predetermined pattern, however, may need the whole time series data to identify characteristics of the waveform. Therefore, the time series of electrical potential data at each lead and a corresponding label of the each lead may need to be used.

The EMG waveform may represent an electrical activity at a predetermined muscle. Electrodes for each muscle may be generally placed at end points of the muscle. That is, each muscle may have a corresponding recommended placement of the electrodes. In addition, classified waveform pattern information of EMG may be absent. The time series of electrical potential data at each muscle and corresponding label of the each muscle may need to be used.

Example embodiments include computer-readable media including program instructions to implement various operations embodied by a computer. The media may also include, alone or in combination with the program instructions, data files, data structures, tables, and the like. The media and program instructions may be those specially designed and constructed for the purposes of example embodiments, or they may be of the kind well known and available to those having skill in the computer software arts. Examples of computer-readable media include magnetic media such as hard disks, floppy disks, and magnetic tape; optical media such as CD ROM discs; magneto-optical media such as floptical discs; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter. The described hardware devices may be configured to act as one or more software modules in order to perform the operations of the above-described example embodiments, or vice versa. Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Further, according to an aspect of the embodiments, any combinations of the described features, functions and/or operations can be provided.

Moreover, the virtual world processing apparatus may include at least one processor to execute at least one of the above-described units and methods.

Although a few example embodiments have been shown and described, the present disclosure is not limited to the described example embodiments. Instead, it would be appreciated by those skilled in the art that changes may be made to these example embodiments without departing from the principles and spirit of the disclosure, the scope of which is defined by the claims and their equivalents.

What is claimed is:

1. A virtual world processing apparatus for enabling interoperability between a virtual world and a real world or interoperability between virtual worlds, the virtual world processing apparatus comprising:
    an input configured to receive an input of sensed information sensed by a bio sensor, the sensed information relating to biometrics of a user in the real world; and
    an adapter configured to adapt the sensed information in accordance with a sensor capability associated with the bio sensor;
    a controller configured to control an experience within the virtual world based on the adapted sensed information, wherein the sensed information comprises linked list information indicating a link data structure element to group the bio sensor.

2. The virtual world processing apparatus of claim 1, wherein the controlling of the experience comprises:
    changing an appearance of an avatar in the virtual world;
    controlling a direction of the avatar in the virtual world;
    adapting an ability of the avatar in the virtual world;
    adapting an attribute of the avatar in the virtual world;
    adapting a status of the avatar in the virtual world;
    influencing an outcome of an interaction of the avatar with the virtual world; or
    generating metadata of a virtual object in the virtual world.

3. The virtual world processing apparatus of claim 1, further comprising:
    a determining unit configured to determine a health of the user, based on the adapted sensed information.

4. The virtual world processing apparatus of claim 1, wherein the bio sensor comprises at least one of a body height sensor, a body weight sensor, a body temperature sensor, a body fat sensor, a blood type sensor, a blood pressure sensor, a blood sugar sensor, a blood oxygen sensor, a heart rate sensor, an electroencephalography (EEG) sensor, an electrocardiography (ECG) sensor, an electromyography (EMG) sensor, an electrooculography (EOG) sensor, a galvanic skin reflex (GSR) sensor, a bio sensor, or an electrograph sensor.

5. The virtual world processing apparatus of claim 1, wherein the sensed information comprises:
   identification (ID) information to identify an identity of the sensed information;
   group ID information to identify an identity of a multi-sensor group including the bio sensor;
   sensor ID reference information to refer to the bio sensor;
   activate information to determine whether the bio sensor operates or not; and
   priority information with respect to another piece of sensed information that shares a same point with the sensed information in a time at which the sensed information is adapted.

6. The virtual world processing apparatus of claim 1, wherein the input receives an input, from the user, of a sensor adaptation preference for controlling a method of adapting the sensed information.

7. The virtual world processing apparatus of claim 1, wherein, when the bio sensor corresponds to a body height sensor, the sensed information comprises at least one of a unit flag, a timestamp, a unit, and a value.

8. The virtual world processing apparatus of claim 1, wherein, when the bio sensor corresponds to a body weight sensor, the sensed information comprises at least one of a unit flag, a timestamp, a unit, and a value.

9. The virtual world processing apparatus of claim 1, wherein, when the bio sensor corresponds to a body temperature sensor, the sensed information comprises at least one of a unit flag, a location flag, a timestamp, a unit, a value, and a location.

10. The virtual world processing apparatus of claim 1, wherein, when the bio sensor corresponds to a body fat sensor, the sensed information comprises at least one of a unit flag, a timestamp, a unit, and a value.

11. The virtual world processing apparatus of claim 1, wherein, when the bio sensor corresponds to a blood type sensor, the sensed information comprises at least one of an ABO type and an Rh type.

12. The virtual world processing apparatus of claim 1, wherein, when the bio sensor corresponds to a blood pressure sensor, the sensed information comprises at least one of a unit flag, a systolic blood pressure flag, a diastolic blood pressure flag, a mean arterial pressure (MAP) flag, a timestamp, a unit, a systolic blood pressure, a diastolic blood pressure, and an MAP.

13. The virtual world processing apparatus of claim 1, wherein, when the bio sensor corresponds to a blood sugar sensor, the sensed information comprises at least one of a unit flag, a timestamp, a unit, and a value.

14. The virtual world processing apparatus of claim 1, wherein, when the bio sensor corresponds to a blood oxygen sensor, the sensed information comprises at least one of a unit flag, a timestamp, a unit, and a value.

15. The virtual world processing apparatus of claim 1, wherein, when the bio sensor corresponds to a heart rate sensor, the sensed information comprises at least one of a unit flag, a timestamp, a unit, and a value.

16. The virtual world processing apparatus of claim 1, wherein, when the bio sensor corresponds to an EEG sensor, the sensed information comprises at least one of a wave pattern flag, a wave pattern, a timestamp, a unit, and an wave value.

17. The virtual world processing apparatus of claim 1, wherein, when the bio sensor corresponds to an ECG sensor, the sensed information comprises at least one of a timestamp, a unit, and an wave value.

18. The virtual world processing apparatus of claim 1, wherein, when the bio sensor corresponds to an EMG sensor, the sensed information comprises at least one of a timestamp, a unit, and an wave value.

19. The virtual world processing apparatus of claim 1, wherein, when the bio sensor corresponds to an EOG sensor, the sensed information comprises at least one of a timestamp, a unit, and an wave value.

20. The virtual world processing apparatus of claim 1, wherein, when the bio sensor corresponds to a GSR sensor, the sensed information comprises at least one of a unit flag, a timestamp, a unit, and an array value.

21. The virtual world processing apparatus of claim 1, wherein, when a type of the bio sensor corresponds to a bio sensor type, the sensed information comprises at least one of a body height flag, a body weight flag, a body temperature flag, a body fat flag, a blood type flag, a blood pressure flag, a blood sugar flag, a blood oxygen flag, a heart rate flag, an EEG flag, an ECG flag, an EMG flag, an EOG flag, a GSR flag, a body height, a body weight, a body temperature, a body fat, a blood type, a blood pressure, a blood sugar, a blood oxygen, a heart rate, an EEG, an ECG, an EMG, an EOG, and a GSR.

22. The virtual world processing apparatus of claim 1, wherein, when the bio sensor corresponds to an electrograph sensor, the sensed information comprises at least one of a timestamp, a waveform label, a wave value, a unit, and a maximum amplitude.

23. The virtual world processing apparatus of claim 1, wherein the sensed information comprises at least one flag, and each of the at least one flag indicates whether the sensed information includes a predetermined field.

24. An operating method of a virtual world processing apparatus for enabling interoperability between a virtual world and a real world or interoperability between virtual worlds, the method comprising:
   receiving, by a processor, an input of sensed information sensed by a bio sensor, the sensed information relating to biometrics of a user in the real world; and
   adapting the sensed information, based on a sensor capability associated with the bio sensor;
   controlling an experience within the virtual world based on the adapted sensed information,
   wherein the sensed information includes linked list information indicating a link data structure element to group the bio sensor.

25. The virtual world processing method of claim 24, wherein the controlling the experience comprises:
   changing an appearance of an avatar in the virtual world;
   controlling a direction of the avatar in the virtual world;
   adapting an ability of the avatar in the virtual world;
   adapting an attribute of the avatar in the virtual world;
   adapting a status of the avatar in the virtual world;
   influencing an outcome of an interaction of the avatar with the virtual world; or
   generating metadata of a virtual object in the virtual world.

26. The virtual world processing method of claim 24, further comprising:

determining a health of the user, based on the adapted sensed information.

27. A non-transitory computer-readable medium comprising a program for instructing a computer to perform the method of claim 24.

28. A method for interacting between a real world and a virtual world, the method comprising:
- sensing information regarding a user in the real world using at least one bio sensor;
- adapting the sensed information based on at least one sensor capability that corresponds to the at least one bio sensor; and
- controlling at least one object in the virtual world based on the adapted sensed information,
- wherein the sensed information includes linked list information indicating a link data structure element to group the bio sensor.

29. The method of claim 28, further comprising displaying, in the virtual world, a health of the user in the real world,
- wherein the health is determined based on the adapted sensed information.

30. The method of claim 28, further comprising controlling a method of adapting the sensed information based on sensor adaptation preference information received from the user.

* * * * *